United States Patent
Kodas et al.

(10) Patent No.: US 6,623,856 B1
(45) Date of Patent: Sep. 23, 2003

(54) DENTAL GLASS POWDERS COMPRISING SPHERICAL GLASS PARTICLES OF SPECIFIC PARTICLE SIZE DISTRIBUTION

(75) Inventors: Toivo T. Kodas, Albuquerque, NM (US); Mark J. Hampden-Smith, Albuquerque, NM (US); Quint H. Powell, Albuquerque, NM (US); James H. Brewster, Alburquerque, NM (US); Daniel J. Skamser, Greenville, SC (US); Klaus Kunze, Albuquerque, NM (US); Paolina Atanassova, Albuquerque, NM (US); Paul Napolitano, Albuquerque, NM (US)

(73) Assignee: Superior MicroPowders LLC, Albuquerque, NM (US)

( * ) Notice: Subject to any disclaimer, the term of this patent is extended or adjusted under 35 U.S.C. 154(b) by 0 days.

(21) Appl. No.: 09/520,488

(22) Filed: Mar. 8, 2000

Related U.S. Application Data

(63) Continuation-in-part of application No. 09/141,394, filed on Aug. 27, 1998.

(51) Int. Cl.⁷ .................................................. B32B 5/16
(52) U.S. Cl. ...................... 428/402; 428/403; 428/405; 428/406
(58) Field of Search ................................ 428/403, 405, 428/406, 402

(56) References Cited

U.S. PATENT DOCUMENTS

| | | | | |
|---|---|---|---|---|
| 2,935,375 A | | 5/1960 | Boucher | 23/2 |
| 3,765,853 A | | 10/1973 | Riebling | 65/18 |
| 4,015,031 A | * | 3/1977 | Reinhardt et al. | 427/213 |
| 4,108,971 A | | 8/1978 | Takumi et al. | 423/428 |
| 4,220,582 A | | 9/1980 | Orlowski et al. | 260/42.28 |
| 4,459,145 A | | 7/1984 | Elsholz | 65/21.3 |
| 4,554,258 A | | 11/1985 | Francel | 501/21 |
| 4,764,497 A | | 8/1988 | Yuasa et al. | 502/235 |
| 4,775,520 A | | 10/1988 | Unger et al. | 423/335 |
| 4,871,489 A | | 10/1989 | Ketcham | 264/9 |
| 4,892,847 A | | 1/1990 | Reinherz | 501/14 |
| 5,061,682 A | | 10/1991 | Aksay et al. | 505/1 |
| 5,063,179 A | | 11/1991 | Menashi et al. | 501/12 |
| 5,110,335 A | | 5/1992 | Miller et al. | 65/3.12 |
| 5,139,875 A | * | 8/1992 | Metzemacher et al. | 428/403 |
| 5,176,732 A | | 1/1993 | Block et al. | 65/21.4 |
| 5,210,057 A | | 5/1993 | Haun et al. | 501/69 |
| 5,213,598 A | | 5/1993 | Silingardi et al. | 65/18.1 |
| 5,236,683 A | | 8/1993 | Nakazawa et al. | 423/335 |
| 5,286,269 A | | 2/1994 | Paschke et al. | 65/18.1 |
| 5,350,782 A | | 9/1994 | Sasaki et al. | 523/116 |
| 5,358,695 A | | 10/1994 | Helble et al. | 423/592 |
| 5,384,306 A | | 1/1995 | Konig et al. | 501/152 |
| 5,585,173 A | | 12/1996 | Kamo et al. | 428/304.4 |
| 5,609,675 A | | 3/1997 | Noritake et al. | 106/35 |
| 5,622,750 A | | 4/1997 | Kilian et al. | 427/163.2 |
| 5,697,992 A | | 12/1997 | Ueda et al. | 51/307 |
| 5,743,930 A | | 4/1998 | Miyake et al. | 65/142 |
| 5,849,055 A | | 12/1998 | Arai et al. | 65/17.3 |
| 5,856,379 A | * | 1/1999 | Shiratsuchi et al. | 523/209 |
| 5,908,660 A | * | 6/1999 | Griffith et al. | 427/220 |
| 5,952,400 A | * | 9/1999 | Hosoi et al. | 523/120 |
| 5,979,185 A | | 11/1999 | Blackwell et al. | 65/17.4 |
| 6,000,241 A | | 12/1999 | Ranade et al. | 65/17.2 |
| 6,174,926 B1 | * | 1/2001 | Menon et al. | 516/100 |
| 6,376,077 B1 | * | 4/2002 | Hiraishi et al. | 428/403 |
| 6,399,037 B1 | * | 6/2002 | Pflug et al. | 423/342 |
| 6,413,638 B1 | * | 7/2002 | Mager et al. | 428/403 |

* cited by examiner

*Primary Examiner*—H. Thi Le
(74) *Attorney, Agent, or Firm*—Marsh Fischmann & Breyfogle LLP

(57) ABSTRACT

Dental glass powders, methods for producing the powders and dental compositions including the glass powders. The powders preferably have a well-controlled particle size, narrow size distribution and a spherical morphology. The method includes forming the particles by a spray pyrolysis technique. The invention also includes dental filler and restorative compositions that include the glass powders.

33 Claims, 25 Drawing Sheets

102 → [AEROSOL GENERATOR 106] → 108 → [FURNACE 110] → 112 → [PARTICLE COLLECTOR 114] → 116

DENTAL GLASS POWDERS COMPRISING SPHERICAL GLASS PARTICLES OF SPECIFIC PARTICLE SIZE DISTRIBUTION

This application is a continuation-in-part application of U.S. patent application No. 09/141,394 filed on Aug. 27, 1998, entitled "GLASS POWDERS, METHODS FOR PRODUCING GLASS POWDERS AND DEVICES FABRICATED FROM SAME".

BACKGROUND OF THE INVENTION

1. Field of the Invention

The present invention relates to dental glass powders having well controlled chemical and morphological properties, as well as methods for producing the dental glass powders. The glass powders are preferably produced by spray pyrolysis of glass precursors to form glass particles having well-controlled chemical and physical properties. The present invention is also directed to compositions for dental filling and restoration that include the glass powders.

2. Description of Related Art

Dental filling and restoration compositions are utilized to repair and fill teeth. Such dental compositions typically include a polymerizable monomer matrix with an inorganic filler, such as a glass, dispersed throughout the matrix.

For example, dental filling compositions are described in U.S. Pat. No. 5,350,782 by Sasaki et al. Sasaki et al. disclose a dental filling composition including a polymerizable monomer and an inorganic filler. The inorganic filler (e.g., amorphous silica) includes 20 to 80 weight percent spherical particles having an average size of 1 to 5 $\mu$m and 80 to 20 weight percent spherical inorganic oxide particles having an average size of 0.05 to 1 $\mu$m. It is also disclosed that the surface of the spherical particles can be treated, such as with a silane compound.

A process for the production of barium-containing silicate dental glass powders is disclosed in U.S. Pat. No. 6,000,241 by Ranade et al. Ranade et al. disclose that these glasses can exhibit the high strength and high refractive index required for dental composites. It is taught that compositions of 50% $SiO_2$, 8% $Al_2O_3$, 9% $B_2O_3$, and 33% BaO are particularly useful for dental compositions. The process includes atomizing a precursor to the glass and pyrolyzing the atomized precursor at a temperature within the range of 1000° C. to 1600° C., such as about 1400° C.

U.S. Pat. No. 5,609,675 by Noritake et al. discloses inorganic compositions containing 60 to 99 weight percent spherical inorganic particles having a mean particle diameter greater than 0.1 $\mu$m but not greater than 1 $\mu$m, and 1 to 40 weight percent inorganic fine particles having a mean particle diameter not greater than 0.1 $\mu$m.

U.S. Pat. No. 4,764,497 by Yuasa et al. discloses a composition including spherical particles of an amorphous composition with a particle size of 0.1 to 1 $\mu$m and a standard deviation of 1.3. Yuasa et al. do not disclose the use of larger particles, such as those greater than about 1 $\mu$m in size.

There remains a need for glass particles for dental filling and restorative compositions and improved methods for making the glass particles.

SUMMARY OF THE INVENTION

One aspect of the present invention is directed to a powder batch of glass particles wherein the glass particles are substantially spherical, have a weight average particle size of not greater than about 5 $\mu$m and a surface area of at least about 3 $m^2/g$. The glass particles advantageously include silane groups attached to an outer surface of the particles wherein the concentration of silane groups is at least about 5, more preferably at least about 7, silane groups per square nanometer of glass surface area. The powder batch can advantageously have a narrow size distribution. In a preferred embodiment, the glass is a barium boroaluminosilicate glass that is useful in dental filling and restorative compositions.

According to another aspect of the present invention, a powder batch of dental glass particles is provided wherein the glass is a barium boroaluminosilicate glass and the particles have an average size of from about 1 $\mu$m to about 5 $\mu$m. The particles are substantially spherical and have a size distribution wherein at least about 80 weight percent of the glass particles have a size of not greater than about 2.5 times the average particle size. The surface area of the glass particles is preferably at least about 3 $m^2/g$ and more preferably is at least about 5 $m^2/g$.

The present invention also provides a method for the production of dental glass particles including the steps of generating an aerosol of droplets of liquid precursors, moving the droplets in a carrier gas and pyrolyzing the droplets at a reaction temperature of from about 1000° C. to 1500° C. to form glass particles having a refractive index of from about 1.40 to about 1.60. The particles are preferably treated to increase the surface area of the particles to enhance their adhesion in a resin matrix.

The present invention also provides a method for the production of dental glass particles including the steps of providing a batch of spherical glass particles having an average size of not greater than about 5 $\mu$m, treating the surface of the glass particles to increase the surface area of the glass particles by at least about 100 percent without substantially altering the bulk morphology of the particles, hydrolyzing the outer surface of the glass particles and then silanating the surface of the glass particles. The glass particles produced by the foregoing method advantageously have a good dispersion and adhesion in a resin matrix when used for a dental composition.

The present invention also provides a dental resin composition including a resin polymer and spherical glass particles dispersed throughout the resin polymer wherein the glass particles have a surface area of at least about 5 $m^2/g$ and wherein the glass particles include a silane concentration of at least about 7 silane groups per square nanometer of glass surface area.

BRIEF DESCRIPTION OF THE DRAWINGS

FIG. 1 is a process block diagram showing one embodiment of the process of the present invention.

DETAILED DESCRIPTION OF THE INVENTION

Figure 2:
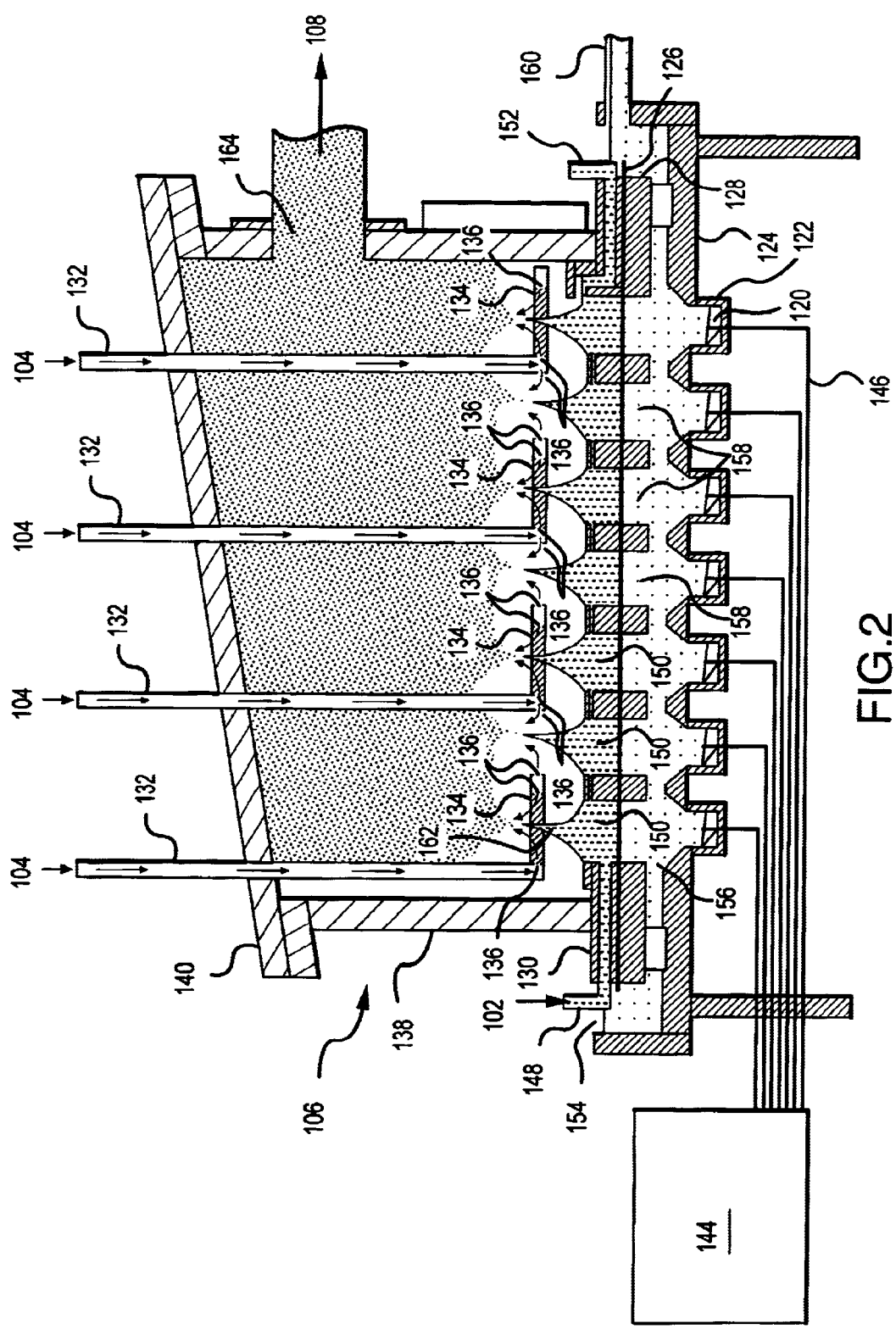
FIG. 2 is a side view in cross section of one embodiment of aerosol generator of the present invention.

The present invention is generally directed to dental glass powders, methods for making dental glass powders and dental filling and restorative compositions including the powders. As used herein, glass powders or glass particles are inorganic compounds in particulate form that are predominately amorphous (non-crystalline) as determined, for example, by x-ray diffraction analysis of the powder. Glasses are characterized by a random structure with no long-range (crystalline) order. However, it will be appreciated, as is discussed below, that it may be advantageous for some applications to intentionally incorporate a second phase, such as a crystalline metal oxide, to form a composite with the glass.

The glass powder batches according to the present invention include a commercially useful quantity of glass particles. The glass particles preferably include at least a first glass phase. According to one embodiment, the glass particles preferably include at least about 80 weight percent glass, more preferably include at least about 90 weight percent glass and even more preferably at least about 95 weight percent glass. In one preferred embodiment, the particles include at least about 99 weight percent glass, that is, not greater than about 1 weight percent of a crystalline phase.

Typically, the dental glass compositions are complex glasses which include binary, ternary or quaternary glasses, as well as glasses including more than four components. The following description of preferred glass compositions is by way of example, and is not intended to limit the present invention to any specific glass composition.

The most common types of glasses are oxide glasses. Oxide glasses can generally be categorized as: silicates, based on $SiO_2$, and including sub-groups such as aluminosilicates; borates, based on $B_2O_3$; phosphates, based on $P_2O_5$; and germanates, based on $GeO_2$. The foregoing oxides ($SiO_2$, $B_2O_3$, $P_2O_5$ and $GeO_2$) are commonly referred to as glass-formers. The structure of the glass based on these oxides can be modified through the addition of intermediate oxides, such as $Al_2O_3$, $Bi_2O_3$ and $PbO$. At high concentrations, these intermediate oxides can also be considered glass-formers. Glass compositions can also be modified by the addition of one or more alkali oxides (e.g., oxides of Li, Na, K, Rb or Cs) and alkaline earth oxides (e.g., oxides of Mg, Ca, Sr or Ba).

Aluminosilicate glasses, which include $SiO_2$ and $Al_2O_3$, are particularly preferred for use in the dental glass compositions according to the present invention. A preferred composition for a dental glass is illustrated in Table 1.

TABLE I

Dental Glass Composition

| Component | Range (wt. %) |
| --- | --- |
| $SiO_2$ | 55–65 |
| $BaO$ | 28–38 |
| $B_2O_3$ | ≤10 |
| $Al_2O_3$ | ≤4 |

In addition to barium boroaluminosilicate (Ba—B—Al—Si—O) glass, other glasses can be used such as calcium boroaluminosilicate (Ca—B—Al—Si—O) and strontium boroaluminosilicate (Sr—B—Al—Si—O) glasses, as well as fluorinated versions of these compositions that additionally include fluorine, such as up to about 4 weight percent fluorine. Other additives to these glasses can include, but are not limited to, Ca, Zn, Sn and Zr. It will be appreciated by those skilled in the art that combinations of the foregoing glasses are also possible.

Other useful compositions include glasses and glass-ceramics based on Mg—Ca—Si—P—B—Al—O with fluorine additions, Si—Ca—P—Na—Al—O, Zr—Si—O, Si—Ca—P—O, Si—P—Na—K—Mg—Ca—O, Si—Ca—Na—P—Ca—B—O, apatites, wollastonites, diopside, crystalline quartz and others. Each of these compositions can also include fluorine. One preferred glass composition is $ZrO_2$—$SiO_2$, such as one including about 30 weight percent $ZrO_2$ and 70 weight percent $SiO_2$.

It is preferred that the dental glass composition has a melting point of not greater than about 1300° C. and more preferably not greater than about 1200° C. Further, it is preferred that the softening point of the glass is not greater than about 1000° C. A low melting point and softening point is advantageous with respect to the process of the present invention, discussed in detail hereinbelow, because it permits more convenient production of particles with good refractive index and low opacity in the resin matrix by reducing the likelihood of forming porous or hollow particles.

It is an advantage of the present invention that the glass composition within the particles can be homogeneous and well mixed on the atomic level and can have substantially no phase segregation of the different phases in the particle. Such a high degree of homogeneity in complex glasses is often not obtainable by traditional forming methods, such as sol-gel or liquid precipitation. However, it may be desirable for some applications that the particles consist of two or more distinct phases, and such a multi-phase composition can also be produced according to the present invention. Further, it may be desirable to have a non-uniform composition throughout the individual particles. Examples include coatings and gradients in the particle composition. In one embodiment, silica ($SiO_2$) is preferentially segregated on the surface of the particles. $SiO_2$ on the particle surface advantageously accommodates more hydroxyl groups ($OH^-$) and therefore a higher degree of surface silanation, as is discussed below. In such an embodiment, the outer layer of $SiO_2$ preferably has an average thickness of not greater than about 10 nanometers.

The dental glass powder according to one embodiment of the present invention includes glass particles having a small average particle size. Although the preferred average size of the particles will vary according to the particular application of the powder, the volume average particle size is preferably at least about 0.1 μm, more preferably is at least about 0.3 μm and even more preferably is at least about 0.5 μm. Further, it is preferred that the volume average particle size of the glass powder is not greater than about 5 μm, more preferably is not greater than about 3 μm and even more preferably is not greater than about 2 μm. In one embodiment, the glass powder has a volume average particle size of from about 0.5 μm to about 2 μm. As used herein, the average particle size is the median particle size ($d_{50}$). Glass powder batches having an average particle size within the preferred parameters disclosed herein enable the formation of dental compositions having high solids loading, good flowability, good optical transparency (for curing of the resin using light) and good wear properties.

According to a preferred embodiment of the present invention, the powder batch of glass particles also has a narrow particle size distribution, such that the majority of glass particles are about the same size. Preferably, at least about 80 weight percent, more preferably at least about 85 weight percent and most preferably at least about 90 weight percent of the particles are not larger than 2.5 times the volume average particle size. Thus, when the average particle size is about 2 μm, it is preferred that at least about 80 weight percent of the particles are not larger than 5 μm. Further, it is preferred that at least about 80 weight percent of the particles are not larger than about 2 times the volume average particle size. In a more preferred embodiment, at least about 85 weight percent, and more preferably at least about 90 weight percent of the particles are not larger than 2 times the average particle size. Thus, when the average particle size is about 2 μm, it is preferred that at least about 80 weight percent of the particles are not larger than 4 μm.

It is also possible according to the present invention to provide a glass powder batch having a bimodal particle size distribution to enhance the packing efficiency of the powder. That is, the powder batch can include particles having two distinct average particle sizes. In this embodiment, the smaller size particles preferably have a volume average size of not greater than about 1 μm, such as from about 0.5 μm to about 1 μm, and the larger size particles preferably have a volume average size of from about 1 μm to about 5 μm, more preferably from about 1 μm to 2 μm. For each of the size distributions it is preferred that at least about 80 weight percent, and more preferably at least about 85 weight percent of the particles are not larger than 2 times the average particle size for that distribution. Bimodal particle size distributions, however, are only useful when they do not substantially degrade other properties of the dental composition. As an example, if the larger size particles are porous or hollow or have the incorrect refractive index then their presence is undesirable. If, however, the larger particles are non-porous with the correct refractive index, then their presence can enhance the powder packing in the resin and improve wear in mechanical properties of the dental composition.

According to yet another embodiment, the as-produced particles have a bimodal particle size distribution wherein the larger particles are agglomerates of smaller primary particles. Milling the powder advantageously forms a monomodal distribution of powder wherein some of the glass particles are non-spherical. Such a glass powder batch can be advantageous for dental compositions where the non-spherical particles enhance the strength of the composite.

The glass powders produced by the processes described hereinbelow, namely spray pyrolysis, can form soft agglomerates as a result of their high surface energy. It is also known that soft agglomerates may be easily dispersed by treatments such as exposure to ultrasound in a liquid medium or sieving. The particle size distributions described herein are measured by mixing samples of the powders in a medium such as water with a surfactant and exposing the suspension to ultrasound using an ultrasonic bath or horn. The ultrasonic treatment supplies sufficient energy to disperse the soft agglomerates into the primary spherical particles. The primary particle size distribution is then measured by light scattering, such as in a Microtrac particle size analyzer (Honeywell Industrial Automation and Control, Fort Washington, Pa.). Thus, the references to particle size herein refer to the primary particle size, such as after lightly dispersing the soft agglomerates of the powder.

The glass particles produced according to the present invention also have a high degree of purity and it is preferred that the particles include not greater than about 0.1 atomic percent impurities and more preferably not greater than about 0.01 atomic percent impurities. According to one preferred embodiment, the glass particles include not greater than about 100 ppm, more preferably not greater than 50 ppm, of metallic impurities that can discolor the glass, such as chromium. It is preferred that the particles have a well-controlled refractive index such that the refractive index of the glass closely matches the refractive index of the resin binder, leading to a low opacity. Even low levels of impurities can adversely alter the refractive index, tint, color or shading of the particles. By controlling the refractive index of the glass particles, the resin composition can be varied which advantageously permits the use of resins with different characteristics. Typically, the glass particle should have a refractive index of from about 1.40 to 1.60, such as from about 1.50 to about 1.55.

According to one embodiment of the present invention, the glass particles are dense (e.g., not hollow or porous), as measured by helium pycnometry. Dense particles are advantageous since hollow or porous particles have a degraded refractive index and degraded opacity, particularly when placed in a resin. According to this embodiment, the glass particles have a particle density of at least about 80% of the theoretical value for the glass compound, more preferably at least about 90% of the theoretical value and even more preferably at least about 95% of the theoretical value. In one embodiment, the particle density is at least about 99% of the theoretical value. The theoretical density can be calculated for glasses based on the relative percentages of each component. High density particles provide many advantages over porous particles, including improved flow properties and improved optical properties.

The glass particles according to a preferred embodiment of the present invention are also substantially spherical in shape. That is, the particles are not jagged or irregular in shape. Spherical particles are particularly advantageous because of the improved flow characteristics imparted to viscous resin systems when loaded with a high percentage of the particles. The resin should remain flowable with loadings in excess of 50 weight percent, more preferably in excess of 60 weight percent, even more preferably in excess of 70 weight percent, and most preferably in excess of 80 weight percent of the spherical glass particles. The high loading level is enabled through the use of spherical particles and is not obtainable with aspherical particles.

In addition, the powder batches of glass particles according to the present invention are substantially unagglomerated, that is, they include substantially no hard agglomerates of the glass particles. Hard agglomerates are physically coalesced lumps of two or more particles that behave as one large particle. It is preferred that no more than about 1.0 weight percent of the glass particles in the powder batch of the present invention are in the form of hard agglomerates and more preferably no more than about 0.5 weight percent of the particles are in the form of hard agglomerates. In the event that some hard agglomerates do form, they can be reduced by lightly milling the powder. Milling is particularly useful when the particles are heated after production to remove moisture and increase the refractive index, which may result in some agglomeration. Milling can be accomplished by using devices such as a jet mill or ball mill. Lightly milling can also increase the surface roughness of the spherical particles which enhances the mechanical bonding of the particles in a resin matrix and provides an increased number of surface sites available for silanation, as is discussed hereinbelow. Wet milling of the particles with the addition of various chemicals can advantageously roughen the particle surface and hydroxylate the particle surface for silanation in the same process step.

The glass particles can also be size separated, such as by passing the particles through a screen with apertures of a known size. In one embodiment, the glass particles are passed through a 270 mesh screen, which has an aperture size of about 53 $\mu$m. Passing the particles through such a screen has the additional advantage that large pieces of foreign material such as gasket material or fibers from a filter bag can be removed.

According to one embodiment of the present invention, the glass particles are composite glass particles, wherein the individual particles include at least a first glass phase and at least a second phase associated with the glass phase. Multi-phase particles can be formed including two or more distinct glass phases. The second phase can also be, for example, a metal or a crystalline metal oxide dispersed in a glass matrix. An example is $SiO_2$, $Al_2O_3$ or $ZrO_2$ polycrystalline particles dispersed in a glass matrix.

According to another embodiment of the present invention, the glass particles are coated particles that include a particulate coating or non-particulate (film) coating that substantially encapsulates the outer surface of the particles. The coating can be a metal, an inorganic compound, or an organic compound. The particles can include more than one coating, if multiple coatings are desirable. However, any such coating should not adversely affect the refractive index or other optical properties of the particles. Preferably, the coating is very thin and has an average thickness of not greater than about 100 nanometers, more preferably not greater than about 50 nanometers, and even more preferably not greater than about 10 nanometers. While the coating is thin, the coating should encapsulate the entire particle such that substantially no glass surface is exposed. Accordingly, the coating preferably has an average thickness of at least about 5 nanometers.

The coating can include, for example, $SiO_2$ which may enable an increased number of hydroxyl groups to attach to the particle surface compared to an uncoated glass particle. The higher number of attached hydroxyl groups can allow improved silanation resulting in better adhesion to the resin matrix. Other advantageous coating materials include $Al_2O_3$ and $ZrO_2$. A particulate coating which consists of a number of ultra-fine particles adhered to the glass particle surface can be advantageous for increasing the surface roughness of the particles, thereby enhancing the mechanical bonding of the particles in the resin matrix.

According to one preferred embodiment of the present invention, the glass particles are coated with a surface modifying agent. The surface modifying agent is typically an organic compound, and a preferred surface modifying agent is a silane compound. The surface modifying agent will provide improved dispersion and improved adhesion in a dental composition that includes a resin.

In a preferred embodiment of the present invention, the glass is first treated to increase the surface area of the glass particles which provides increased surface area for the attachment of the surface modifying agent. After treatment to increase the surface area, the glass particles can then be treated to provide chemical attachment groups, such as hydroxyl groups, for the surface modifying agents. The hydroxyl groups on the particle surface can then be reacted with the surface modifying agent which cross-links with the resin during polymerization. Improving the level of chemical and mechanical bonding between the glass particles and the resin improves the wear resistance of the cured dental composite.

The surface area of the glass can be increased in a number of different ways such as by chemical etching (e.g., dissolution) of some or all of the surface chemical species, mechanical abrading of the surface, such as jet-milling or other soft milling steps or methods which employ a combination of these processes such as high pressure water or ball milling. The goal is to cause roughening of the surface at the nanometer scale to slightly increase the surface area while not interfering with the morphological benefits of the spherical glass or degrading the optical opacity in a resin matrix. The chemical etching may be achieved by acid or base catalysis wherein the glass particles are contacted with an acidic or basic solution. The acids may be either inorganic acids such as HF, $H_2SiF_6$, nitric acid, aqua regia and the bases can be, for example, KOH, NaOH or $NH_3OH$. Chemical etching of complex glass particles occurs due to the preferential etching by the acid or base of one surface species over another. It has been found that treating the particles in an acid or a base also enhances the opacity of filler compositions containing the particles, probably due to the removal of surface impurities.

The glass particles of the present invention are initially smooth and dense and therefore have a low surface area, such as less than about 2 $m^2/g$. The surface treatment can advantageously increase the surface area of the glass particles to at least about 3 $m^2/g$ more preferably to at least about 4 $m^2/g$, even more preferably to at least about 5 $m^2/g$ and most preferably to at least about 10 $m^2/g$. In one embodiment, the particles have a surface area of at least about 20 $m^2/g$. The surface treatment parameters such as time, temperature and concentration of the acid or base can be controlled to obtain the desired surface area.

In one embodiment, the treatment increases the surface area of the particles by at least about 50%, more preferably by at least about 100% and even more preferably by at least about 200%. In one embodiment, the surface area increases by at least 500%. According to the present invention, the surface treatment advantageously increases the surface area of the particles without substantially affecting the original spherical morphology of the particles.

Surface area is typically measured using the BET nitrogen adsorption method which is indicative of the surface area of the powder, including the surface area of accessible pores on the surface of the particles. As is discussed above, the as-produced glass particles have a relatively low surface area since the particles are spherical and non-porous. It is an advantage of the present invention that spherical, non-porous particles are treated to increase the surface area of the particles to enhance their bonding in a resin matrix.

The chemical, mechanical or chemical/mechanical roughening of this surface can also simultaneously increase the level of surface hydroxylation by, for example, etching the particles under conditions where the hydroxyl group formation is maximized, for example by chemical etching in the presence of a base such as KOH or acids such as HF or $H_2SiF_6$. Thus, the two steps of increasing the surface area and increasing the level of hydroxylation can advantageously be achieved in a single step.

The chemical attachment groups may include a variety of different chemical species such as hydroxyl groups in the case of metal oxides in the glass or halide groups (e.g., F) in the case of metal halides in the glass. For example, surface hydroxyl groups on a metal oxide glass particle can be reacted with a vinyl organosilane surface modifying agent that converts the hydroxyl group functionality to a vinyl group functionality. The vinyl functional group is then capable of cross linking with the vinyl groups in the resin under irradiation with light.

The as-produced spherical glass particles may have a surface concentration of chemical attachment groups, such as surface hydroxyl groups, that is much less than the maximum number possible. Using metal oxides as an example, the number of surface hydroxyl groups per unit surface area may advantageously be increased by exposing the glass to an aqueous environment either as a gas phase or, more preferably, as a liquid. For example, the powder can be placed in deionized water for a sufficient amount of time, e.g., about an hour, filtered and dried to remove physically adsorbed water. The presence of either an acid or base catalyst may reduce the time required for the hydroxylation reaction, as will increased temperature. An example of the reaction to convert a metal oxide on the surface to a metal hydroxide is illustrated in Equation 1.

$$M\text{---}O\text{---}M + H_2O \rightarrow 2MOH \tag{1}$$

The glass particles can include more than one metal oxide component and there is a high probability that a number of different metal oxides will form different metal hydroxide groups on the surface of the particles. For example, in the case of Ba—B—Al—Si—O glass, each of the metal oxide species (Al, Si, B and Ba) may have a different reaction rate with water to form the metal hydroxide. In addition, each metal oxide can exhibit a number of different types of surface hydroxyl groups such as isolated, viscinal, geminal and hydrogen-bonded surface hydroxyl groups as well as hydroxyl groups of hydrogen-bonded water. All these different surface hydroxyl groups have different reactivities toward other reagents such as the surface modifying reagents (e.g., organosilanes).

In the specific case of Ba—B—Al—Si—O glass prepared by spray pyrolysis (discussed below), it has been found that the surface of the glass particles can have a different composition to that of the bulk glass. This may be beneficial for control over the level and number of surface hydroxyl groups. For example, in one embodiment of the present invention, the Ba—B—Al—Si—O glass particles have a surface composition that is almost exclusively $SiO_2$. Since $SiO_2$ accommodates a high number of surface hydroxyl groups per unit surface area, the $SiO_2$-rich layer is beneficial for surface hydroxylation.

The higher the level of surface modifying agents on the glass surface per unit mass, the higher the wear resistance of the final dental composition. Therefore, it is advantageous to maximize the number of surface modifying agents that can attach to the glass by increasing the number of chemical attachment groups (e.g., surface hydroxyl groups) by chemical treatment and by increasing the surface area. The surface hydroxyl groups can then be reacted with a silanating agent which can chemically bond to the hydroxyl groups on the glass surface by elimination of a small organic molecule HX, where X is a halide, amide or alkoxide. The silanating agent then contains a different functional group that can effect a chemical reaction with the resin during the curing process. Such derivatizing or modification reagents are characterized according to the following reaction.

$$\text{Glass} - X + \begin{bmatrix} Y \\ Y \\ Y \end{bmatrix}_A E \quad [-R'-Z]_{B-A} \quad (2)$$

In the foregoing equation, X can be chosen from OH or a halide. Y can be chosen from a halide, an alkoxide (OR where R=alkyl, aryl or derivatives thereof, an amide ($NR_2$ where R=alkyl, aryl or derivatives thereof) or a carboxylate. E can be chosen from Si, Ge, Ti,Zr or C.

R' can be chosen from alkyl groups, aryl groups or derivatives thereof, for example ethers or amines. The species R' may also contain a group R'' with a similar or different functionality as Z, to provide better bonding to the resin or to provide a time release of another species such as fluoride (e.g., on hydrolysis in the mouth). Z can be selected from vinyl, carboxylates, amides, amines, methacrylates, amino acids or fluorides.

The integral values of A and B may vary from 0 to 4, wherein A+B=4. It is better to have A>B if wear primarily occurs at the chemical bonding of the surface of the glass. But the reverse is true and B>A is useful if there is a stronger chemical cross link to the resin.

Thus, the glass particles are preferably treated to increase the surface area which is available for attachment of the surface modifying agents. The increased surface area is particularly advantageous when the particles are substantially spherical. The treatment to form chemical attachment groups such as hydroxyl groups advantageously can form at least about 5 hydroxyl groups per square nanometer, more preferably at least about 7 hydroxyl groups per square nanometer and even more preferably at least about 10 hydroxyl groups per square nanometer. It is believed that the maximum number of hydroxyl groups the surface can accommodate is about 13 hydroxyl groups per square nanometer, and in a particularly preferred embodiment, the particles have a concentration of about 13 hydroxyl groups per square nanometer. The foregoing treatment thereby enables a high degree of surface modifying agents to be attached to the particles.

Preferably, the glass particles include a concentration of silane groups of at least about 5 silane groups per square nanometer of glass surface area, more preferably at least about 7 silane groups per square nanometer of glass surface area and even more preferably at least about 10 silane groups per square nanometer of glass surface area. In one embodiment, the concentration of silane groups is from about 5 to about 13 silane groups per square nanometer, more preferably from about 7 to about 13 silane groups per square nanometer and even more preferably from about 10 to about 13 silane groups per square nanometer. On a mass basis, the glass particles preferably include not greater than about 4 weight percent, more preferably not greater than about 3 weight percent of silane based on the mass of the glass particles. The method of the present invention advantageously enables the formation of glass particles with a high surface concentration of silane groups while keeping the overall amount of silane low. That is, excess silane is not necessary.

The surface coating can be comprised of one or more monolayer coatings, such as from about 1 to 3 monolayer coatings. A monolayer coating is formed by the reaction of an organic or an inorganic molecule with the surface of the particles to form a coating layer that is essentially one molecular layer thick. In particular, the formation of a monolayer coating by reaction of the surface of the particle with the functionalized organo silane such as halo- or amino-silanes, for example hexamethyldisilazane or trimethylsilylchloride, can be used to modify the hydrophobicity and hydrophilicity of the powders. A preferred silane group according to the present invention is a methacryl-functional silane such as gamma-methacryloxypropyltrimethoxysilane. An example of such a silane group is SILQUEST A-174 silane (Witco Corp., Friendly, W.Va.).

In one aspect, the present invention provides a method for preparing a particulate product including a glass. A liquid feed, including at least one precursor for the glass, is converted to aerosol form, with droplets of the medium being dispersed in and suspended by a carrier gas. Liquid from the droplets in the aerosol is then removed to permit formation in a dispersed state of the desired glass particles. Typically, the feed precursor is pyrolyzed in a furnace to form the glass particles. In one embodiment, the particles are subjected, while still in a dispersed state, to compositional or structural modification, if desired. Compositional modification may include, for example, coating the particles as is discussed above. Structural modification may include, for example, annealing the particles. The term powder is often used herein to refer to the particulate product of the present invention. The use of the term powder does not indicate, however, that the particulate product must be dry or in any particular environment. Although the particulate product is typically manufactured in a dry state, the particulate product may, after manufacture, be placed in a wet environment, such as in a slurry.

The process of the present invention is particularly well suited for the production of finely divided glass particles having a small weight average size. In addition to making particles within a small weight average particle size, the particles may be produced with a narrow size distribution, thereby providing size uniformity that is desired for many applications such as dental compositions.

The method of the present invention also provides significant flexibility for producing particles of varying chemical composition wherein the particles are high purity with good chemical homogeneity. Complex glasses, such as binary, ternary or quaternary glasses, can be formed by the present method. The ability to tightly control the chemical composition of the glass particles advantageously permits control over the properties of the glass such as glass transition temperature ($T_g$), density, opacity and the like. The method also permits the formation of glass composites, as is discussed above.

Referring now to FIG. 1, one embodiment of the process of the present invention is described. A liquid feed 102, including at least one precursor for the desired glass particles, and a carrier gas 104 are fed to an aerosol generator 106 where an aerosol 108 is produced. The aerosol 108 is then fed to a furnace 110 where liquid in the aerosol 108 is removed to produce glass particles 112 that are dispersed in and suspended by gas exiting the furnace 110. The glass particles 112 are then collected in a particle collector 114 to produce a particulate product 116.

As used herein, the liquid feed 102 is a feed that includes one or more flowable liquids as the major constituent(s), such that the feed is a flowable medium. The liquid feed 102 need not comprise only liquid constituents. The liquid feed 102 may comprise only constituents in one or more liquid phase, or it may also include particulate material suspended in a liquid phase. The liquid feed 102 must, however, be capable of being atomized to form droplets of sufficiently small size for preparation of the aerosol 108. Therefore, if the liquid feed 102 includes suspended particles, such as colloidal silica particles, those particles should be relatively small in relation to the size of droplets in the aerosol 108. Such suspended particles should typically be smaller than about 1 $\mu$m in size, preferably smaller than about 0.5 $\mu$m in size, and more preferably smaller than about 0.3 $\mu$m in size and most preferably smaller than about 0.1 $\mu$m in size. The suspended particles could be finely divided particles, or could consist of agglomerated smaller primary particles. For example, 0.5 $\mu$m particles could be agglomerates of nanometer-sized primary particles. When the liquid feed 102 includes suspended particles, the particles preferably comprise not greater than about 15 weight percent, more preferably not greater than about 10 weight percent, and most preferably not greater than about 5 weight percent of the liquid feed.

As noted, the liquid feed 102 includes at least one precursor for preparation of the glass particles 112. The precursor may be a substance in either a liquid or solid phase of the liquid feed 102. Preferably, the precursor will include a material dissolved in a liquid solvent of the liquid feed 102, such as a metal salt. The precursor can also be an acid, such as boric acid ($H_3BO_3$), a precursor to $B_2O_3$. The precursor may undergo one or more chemical reactions in the furnace 110 to assist in production of the particles 112. Alternatively, the precursor material may contribute to formation of the particles 112 without undergoing chemical reaction. This could be the case, for example, when the liquid feed 102 includes suspended $SiO_2$ particles that are not chemically modified in the furnace 110. In any event, the particles 112 comprise at least one component originally contributed by the precursor. One of the advantages of the present invention is that high quality glass powders can be produced from reasonably inexpensive precursor materials.

The liquid feed 102 thus includes the chemical components that will form the glass particles 112. For example, the liquid feed 102 can comprise a solution containing nitrates, acetates, chlorides, sulfates, hydroxides, or oxalates of a metal. Particularly preferred precursor salts include metal nitrates and metal acetates. These salts are typically highly soluble in water and the solutions maintain a low viscosity. For some glass components, metal nitrates are preferred since they do not contain any carbon that can potentially contaminate the end-product. For example, aluminum nitrate is a preferred precursor to $Al_2O_3$. It may be desirable to acidify the solution to increase the solubility of the precursors, such as by adding nitric acid or hydrochloric acid. It may also be desirable to modify the pH of the solution to ensure that suspended solid particulates remain well dispersed in the suspension. Acids can also be used as precursors, such as boric acid ($H_3BO_3$) as a precursor to $B_2O_3$.

Partially or completely hydrolyzed metal alkoxides can also be used as reactants. Examples include partially or completely hydrolyzed alkoxides of silicon, aluminum and barium which can form small particles containing silicon, aluminum and barium bonded to oxygen and then to other metal atoms. Alkoxide precursors can also be used for $ZrO_2$, such as in a $ZrO_2$—$SiO_2$ glass composition. Examples of such alkoxides include Al-butoxides, Si-ethoxides and molecules with larger ligands.

The solution preferably has a precursor concentration that is unsaturated to avoid the possibility of undesirable precipitate formation. The solution preferably includes a soluble precursor to yield a concentration of from about 1 to 20 weight percent of the glass composition and even more preferably from about 3 to about 15 weight percent of the glass composition, such as about 5 to 7.5 weight percent of the glass composition. The final particle size of the glass particles 112 is also influenced by the precursor concentration. Generally, lower precursor concentrations will yield glass particles having a smaller average particle size.

The precursor mixture consisting of precursor particles and/or soluble precursors can be heated to sufficiently mix the precursors or, preferably, can be agitated without substantial heating to form a precursor solution suitable for use in the process of the present invention.

The carrier gas 104 may comprise any gaseous medium in which droplets produced from the liquid feed 102 may be dispersed in aerosol form. The carrier gas 104 may be inert, in that the carrier gas 104 does not participate in formation of the particles 112. Alternatively, the carrier gas may have one or more active component(s) that contribute to formation of the particles 112. In that regard, the carrier gas may include one or more reactive components that react in the furnace 110 to contribute to formation of the glass particles 112. For example, oxygen can be a reactive component to the formation of oxide glass particles and therefore air is a preferred carrier gas for the formation of metal oxide glass particles.

The aerosol generator 106 atomizes the liquid feed 102 to form droplets in a manner to permit the carrier gas 104 to sweep the droplets away to form the aerosol 108. An important aspect of the present invention is generation of the aerosol 108 with droplets of a small average size and narrow size distribution. In this manner, the glass particles 112 may be produced at a desired small size with a narrow size distribution, which are advantageous for many applications.

The aerosol generator 106 is preferably capable of producing the aerosol 108 such that it includes droplets having a weight average size in a range having a lower limit of about 1 $\mu$m and preferably about 2 $\mu$m; and an upper limit of about 20 $\mu$m; preferably about 10 $\mu$m, more preferably about 7 $\mu$m and most preferably about 5 $\mu$m. A weight average droplet size in a range of from about 2 $\mu$m to about 4 $\mu$m is particularly preferred. The aerosol generator is also preferably capable of producing the aerosol 108 such that it includes droplets in a narrow size distribution. Preferably, the droplets in the aerosol are such that at least about 70 weight percent (more preferably at least about 80 weight percent and most preferably at least about 85 weight percent) of the droplets are smaller than about 10 $\mu$m and more preferably at least about 70 weight percent (more preferably at least about 80 weight percent and most preferably at least about 85 weight percent) are smaller than about 5 $\mu$m. Furthermore, preferably no greater than about 40 weight percent, more preferably no greater than about 30 weight percent and most preferably no greater than about 25 weight percent, of the droplets in the aerosol 108 are larger than about twice the weight average droplet size.

Another important aspect of the present invention is that the aerosol 108 may be generated without consuming excessive amounts of the carrier gas 104. The aerosol generator 106 is capable of producing the aerosol 108 such that it has a high loading, or high concentration, of the liquid feed 102 in droplet form. In that regard, the aerosol 108 preferably includes greater than about $1 \times 10^5$ droplets per cubic centimeter of the aerosol 108, more preferably greater than about $3 \times 10^5$ droplets per cubic centimeter, even more preferably greater than about $1\times10^6$ droplets per cubic centimeter, and even more preferably greater than about $5\times10^6$ droplets per cubic centimeter. That the aerosol generator 106 can produce such a heavily loaded aerosol 108 is particularly surprising considering the high quality of the aerosol 108 with respect to small average droplet size and narrow droplet size distribution. Typically, droplet loading in the aerosol is such that the volumetric ratio of liquid feed 102 to carrier gas 104 in the aerosol 108 is larger than about 0.04 milliliters of liquid feed 102 per liter of carrier gas 104 in the aerosol 108, preferably larger than about 0.083 milliliters of liquid feed 102 per liter of carrier gas 104 in the aerosol 108, and even more preferably larger than about 0.167 milliliters of liquid feed 102 per liter of carrier gas 104.

This capability of the aerosol generator 106 to produce a heavily loaded aerosol 108 is even more surprising given the high droplet output rate of which the aerosol generator 106 is capable, as discussed more fully below. It will be appreciated that the concentration of liquid feed 102 in the aerosol 108 will depend upon the specific components and attributes of the liquid feed 102 and, particularly, the size of the droplets in the aerosol 108. For example, when the average droplet size is from about 2 μm to about 4 μm, the droplet loading is preferably larger than about 0.05 milliliters of aerosol feed 102 per liter of carrier gas 104, more preferably larger than about 0.10 milliliters of liquid feed 102 per liter of carrier gas 104, and even more preferably larger than about 0.15 milliliters of liquid feed 102 per liter of carrier gas 104. When reference is made herein to liters of carrier gas 104, it refers to the volume that the carrier gas 104 would occupy under conditions of standard temperature and pressure.

The loading of the aerosol can be increased, in the context of the apparatus design discussed herein, by operating without a membrane between the water bath and the precursor mixture. That is, the precursor mixture is contacted directly with the ultrasonic transducers.

The furnace 110 may be any suitable device for heating the aerosol 108 to evaporate liquid from the droplets of the aerosol 108 and thereby permit formation of the glass particles 112. The maximum average stream temperature, or reaction temperature, refers to the maximum average temperature that an aerosol stream attains while flowing through the furnace. Although it is possible to pre-dry the droplets before delivering the droplets to the furnace section, but this is not necessary for the production of high quality glass material.

For the production of glass particles, residence time in the heating zone of the furnace 110 will depend on the composition of the glass particles, the reaction temperature, the geometric size of the reactor, the carrier gas flow rate and the aerosol loading which influences the partial pressure of the water vapor. The residence time should be long enough, however, to assure that the particles 112 attain the desired maximum stream temperature for a given heat transfer rate such that substantially all of the precursors are fully reacted. In that regard, with extremely short residence times, higher furnace temperatures could be used to increase the rate of heat transfer so long as the particles 112 attain a maximum temperature within the desired stream temperature range. Also, it is preferred that, in most cases, the maximum stream temperature not be attained in the furnace 110 until substantially at the end of the heating zone in the furnace 110. For example, the heating zone will often include a plurality of heating sections that are each independently controllable. The maximum stream temperature should typically not be attained until the final heating section, and more preferably until substantially at the end of the last heating section. This is important to reduce the potential for thermophoretic losses of material. Also, it is noted that as used herein, residence time refers to the actual time for a material to pass through the relevant process equipment. In the case of the furnace, this includes the effect of increasing velocity with gas expansion due to heating.

Typically, the furnace 110 will be a tube-shaped furnace, so that the aerosol 108 moving into and through the furnace does not encounter sharp edges on which droplets could collect. Loss of droplets to collection at sharp surfaces results in a lower yield of particles 112. Further, the accumulation of liquid at sharp edges can result in re-release of undesirably large droplets back into the aerosol 108, which can cause contamination of the particulate product 116 with undesirably large particles. Also, over time, such liquid collection at sharp surfaces can cause fouling of process equipment, impairing process performance.

The furnace 110 may include a heating tube made of any suitable material. The tube material may be a ceramic material, for example, mullite, fused silica, quartz or alumina. Alternatively, the tube may be metallic. Advantages of using a metallic tube are low cost, ability to withstand steep temperature gradients and large thermal shocks, machinability and weldability, and ease of providing a seal between the tube and other process equipment. Disadvantages of using a metallic tube include limited operating temperature and increased reactivity in some reaction systems. For example, some metal tubes can out-gas chromium at increased temperatures and very small amounts of chromium (e.g., as little as 150 ppm) can discolor the glass particles. Given the foregoing, the proper tube can be selected for a particular glass composition and reactor temperature. For making high purity glass particles, fused silica (quartz) tubes are often preferred.

According to the present invention, the reaction temperature in the heating zone is preferably near or above the softening point of the glass composition to produce a dense material. Although the preferred temperature can vary for different glass compositions, it is generally preferred that the maximum reaction temperature is from about 300° C. to about 1500° C., and more preferably from about 1000° C. to about 1500° C., such as from about 1000° C. to about 1300° C. In a particularly preferred embodiment, a Ba—B—Al—Si—O glass is formed by heating at a reaction temperature of from about 1150° C. to about 1250° C.

Depending on the reaction temperature, the residence time in the heating zone can vary. It is preferred however that the residence time be at least about 2 seconds and typically no more than about 15 seconds. According to one embodiment, the total residence time is between from about 2 to 5 seconds. It is often preferred that the parameters are adjusted to ensure that volatile components such as boric acid do not volatilize.

Also, although the present invention is described with primary reference to a furnace reactor, which is preferred, it should be recognized that, except as noted, any other thermal reactor can be used, including a flame reactor or a plasma reactor. A furnace reactor is preferred, because of the generally even heating characteristic of a furnace for attaining a uniform stream temperature.

The particle collector 114, may be any suitable apparatus for collecting glass particles 112 to produce the particulate product 116. One embodiment of the particle collector 114 uses one or more filters to separate the glass particles 112 from the gas. Such a filter may be of any type, including a bag filter. Another preferred embodiment of the particle collector uses one or more cyclones to separate the particles 112. A cyclone is preferred according to one embodiment of the present invention due to the ability of a cyclone to separate the glass powder based upon particle size. Thus, the collected particles can advantageously have an even narrower particle size distribution. Other apparatus that may be used in the particle collector 114 include an electrostatic precipitator. Collection should normally occur at a temperature above the condensation temperature of the gas stream in which the glass particles 112 are suspended. Also, collection should normally be at a temperature that is low enough to prevent significant agglomeration of the glass particles 112, that is, the temperature should be below the softening point of the glass.

Figure 3:
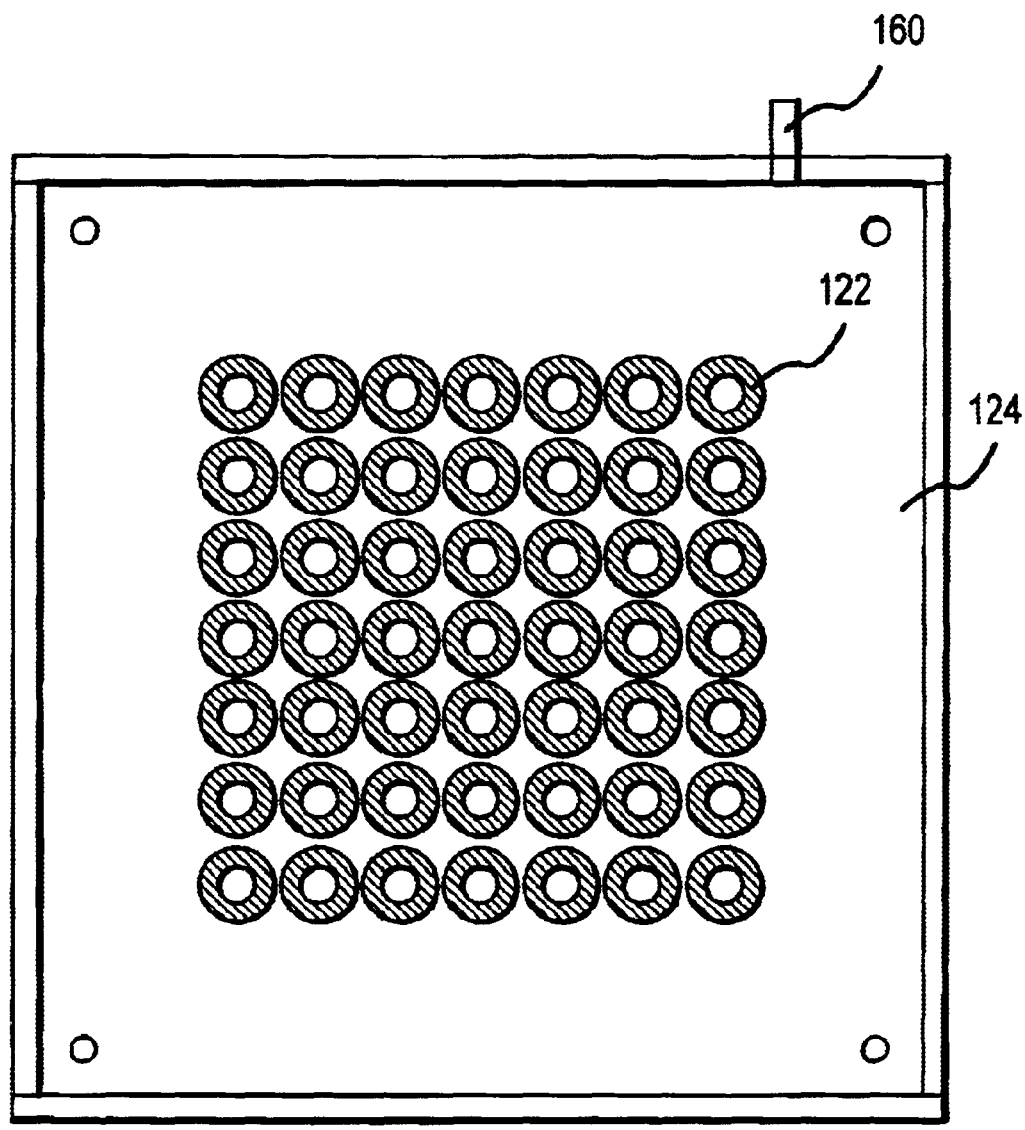
FIG. 3 is a top view of a transducer mounting plate showing a 49 transducer array for use in an aerosol generator of the present invention.

Of significant importance to the operation of the process of the present invention is the aerosol generator 106, which must be capable of producing a high quality aerosol with high droplet loading, as previously noted. With reference to FIG. 2, one embodiment of an aerosol generator 106 of the present invention is described. The aerosol generator 106 includes a plurality of ultrasonic transducer discs 120 that are each mounted in a transducer housing 122. The transducer housings 122 are mounted to a transducer mounting plate 124, creating an array of the ultrasonic transducer discs 120. Any convenient spacing may be used for the ultrasonic transducer discs 120. Center-to-center spacing of the ultrasonic transducer discs 120 of about 4 centimeters is often adequate. The aerosol generator 106, as shown in FIG. 2, includes forty-nine transducers in a 7×7 array. The array configuration is as shown in FIG. 3, which depicts the locations of the transducer housings 122 mounted to the transducer mounting plate 124.

With continued reference to FIG. 2, a separator 126, in spaced relation to the transducer discs 120, is retained between a bottom retaining plate 128 and a top retaining plate 130. Gas delivery tubes 132 are connected to gas distribution manifolds 134, which have gas delivery ports 136. The gas distribution manifolds 134 are housed within a generator body 138 that is covered by generator lid 140. A transducer driver 144, having circuitry for driving the transducer discs 120, is electronically connected with the transducer discs 120 via electrical cables 146.

During operation of the aerosol generator 106, as shown in FIG. 2, the transducer discs 120 are activated by the transducer driver 144 via the electrical cables 146. The transducers preferably vibrate at a frequency of from about 1 MHz to about 5 MHz, more preferably from about 1.5 MHz to about 3 MHz. Commonly used frequencies are at about 1.6 MHz and about 2.4 MHz. Furthermore, all of the transducer discs 110 should be operating at substantially the same frequency when an aerosol with a narrow droplet size distribution is desired. This is important because commercially available transducers can vary significantly in thickness, sometimes by as much as 10%. It is preferred, however, that the transducer discs 120 operate at frequencies within a range of 5% above and below the median transducer frequency, more preferably within a range of 2.5%, and most preferably within a range of 1%. This can be accomplished by careful selection of the transducer discs 120 so that they all preferably have thicknesses within 5% of the median transducer thickness, more preferably within 2.5%, and most preferably within 1 %.

Liquid feed 102 enters through a feed inlet 148 and flows through flow channels 150 to exit through feed outlet 152. An ultrasonically transmissive fluid, typically water, enters through a water inlet 154 to fill a water bath volume 156 and flow through flow channels 158 to exit through a water outlet 160. A proper flow rate of the ultrasonically transmissive fluid is necessary to cool the transducer discs 120 and to prevent overheating of the ultrasonically transmissive fluid. Ultrasonic signals from the transducer discs 120 are transmitted, via the ultrasonically transmissive fluid, across the water bath volume 156, and ultimately across the separator 126, to the liquid feed 102 in flow channels 150.

The ultrasonic signals from the ultrasonic transducer discs 120 cause atomization cones 162 to develop in the liquid feed 102 at locations corresponding with the transducer discs 120. Carrier gas 104 is introduced into the gas delivery tubes 132 and delivered to the vicinity of the atomization cones 162 via gas delivery ports 136. Jets of carrier gas exit the gas delivery ports 136 in a direction so as to impinge on the atomization cones 162, thereby sweeping away atomized droplets of the liquid feed 102 that are being generated from the atomization cones 162 and creating the aerosol 108, which exits the aerosol generator 106 through an aerosol exit opening 164.

Efficient use of the carrier gas 104 is an important aspect of the aerosol generator 106. The embodiment of the aerosol generator 106 shown in FIG. 2 includes two gas exit ports per atomization cone 162, with the gas ports being positioned above the liquid medium 102 over troughs that develop between the atomization cones 162, such that the exiting carrier gas 104 is horizontally directed at the surface of the atomization cones 162, thereby efficiently distributing the carrier gas 104 to critical portions of the liquid feed 102 for effective and efficient sweeping away of droplets as they form about the ultrasonically energized atomization cones 162. Furthermore, it is preferred that at least a portion of the opening of each of the gas delivery ports 136, through which the carrier gas exits the gas delivery tubes, should be located below the top of the atomization cones 162 at which the carrier gas 104 is directed. This relative placement of the gas delivery ports 136 is very important to efficient use of carrier gas 104. Orientation of the gas delivery ports 136 is also important. Preferably, the gas delivery ports 136 are positioned to horizontally direct jets of the carrier gas 104 at the atomization cones 162. The aerosol generator 106 permits generation of the aerosol 108 with heavy loading with droplets of the carrier liquid 102, unlike aerosol generator designs that do not efficiently focus gas delivery to the locations of droplet formation.

Another important feature of the aerosol generator 106, as shown in FIG. 2, is the use of the separator 126, which protects the transducer discs 120 from direct contact with the liquid feed 102, which is often highly corrosive. The height of the separator 126 above the top of the transducer discs 120 should normally be kept as small as possible, and is often in the range of from about 1 centimeter to about 2 centimeters. The top of the liquid feed 102 in the flow channels above the tops of the ultrasonic transducer discs 120 is typically in a range of from about 2 centimeters to about 5 centimeters, whether or not the aerosol generator includes the separator 126, with a distance of about 3 to 4 centimeters being preferred. Although the aerosol generator 106 could be made without the separator 126, in which case the liquid feed 102 would be in direct contact with the transducer discs 120, the highly corrosive nature of the liquid feed 102 can often cause premature failure of the transducer discs 120. The use of the separator 126, in combination with use of the ultrasonically transmissive fluid in the water bath volume 156 to provide ultrasonic coupling, significantly extends the life of the ultrasonic transducers 120. One disadvantage of using the separator 126, however, is that the rate of droplet production from the atomization cones 162 is reduced, often by a factor of two or more, relative to designs in which the liquid feed 102 is in direct contact with the ultrasonic transducer discs 102. Even with the separator 126, however, the aerosol generator 106 used with the present invention is capable of producing a high quality aerosol with heavy droplet loading, as previously discussed. Suitable materials for the separator 126 include, for example, polyamides (such as Kapton™ membranes from DuPont) and other polymer materials, glass, and plexiglass. The main requirements for the separator 126 are that it be ultrasonically transmissive, corrosion resistant and impermeable.

One alternative to using the separator 126 is to bind a corrosion-resistant protective coating onto the surface of the ultrasonic transducer discs 120, thereby preventing the liquid feed 102 from contacting the surface of the ultrasonic transducer discs 120. When the ultrasonic transducer discs 120 have a protective coating, the aerosol generator 106 will typically be constructed without the water bath volume 156 and the liquid feed 102 will flow directly over the ultrasonic transducer discs 120. Examples of such protective coating materials include platinum, gold, TEFLON™, epoxies and various plastics. Such a coating can significantly extend the transducer life. Also, when operating without the separator 126, the aerosol generator 106 will typically produce the aerosol 108 with a much higher droplet loading than when the separator 126 is used.

One surprising finding with operation of the aerosol generator 106 of the present invention is that the droplet loading in the aerosol may be affected by the temperature of the liquid feed 102. It has been found that when the liquid feed 102 includes an aqueous liquid at an elevated temperature, the droplet loading increases significantly. The temperature of the liquid feed 102 is preferably higher than about 30° C., more preferably higher than about 35° C. and most preferably higher than about 40° C. If the temperature becomes too high, however, it can have a detrimental effect on droplet loading in the aerosol 108. Therefore, the temperature of the liquid feed 102 from which the aerosol 108 is made should generally be lower than about 50° C., and preferably lower than about 45° C. The liquid feed 102 may be maintained at the desired temperature in any suitable fashion. For example, the portion of the aerosol generator 106 where the liquid feed 102 is converted to the aerosol 108 could be maintained at a constant elevated temperature. Alternatively, the liquid feed 102 could be delivered to the aerosol generator 106 from a constant temperature bath maintained separate from the aerosol generator 106. When the ultrasonic generator 106 includes the separator 126, the ultrasonically transmissive fluid adjacent the ultrasonic transducer discs 120 is preferably maintained at a temperature not greater than about 30° C.

The design for the aerosol generator 106 based on an array of ultrasonic transducers is versatile and is easily modified to accommodate different generator sizes for different specialty applications. The aerosol generator 106 may be designed to include a plurality of ultrasonic transducers in any convenient number. Even for smaller scale production, however, the aerosol generator 106 preferably has at least nine ultrasonic transducers, more preferably at least 16 ultrasonic transducers, and even more preferably at least 25 ultrasonic transducers. For larger scale production, however, the aerosol generator 106 includes at least 40 ultrasonic transducers, more preferably at least 100 ultrasonic transducers, and even more preferably at least 400 ultrasonic transducers. In some large volume applications, the aerosol generator may have at least 1000 ultrasonic transducers.

Figure 4:
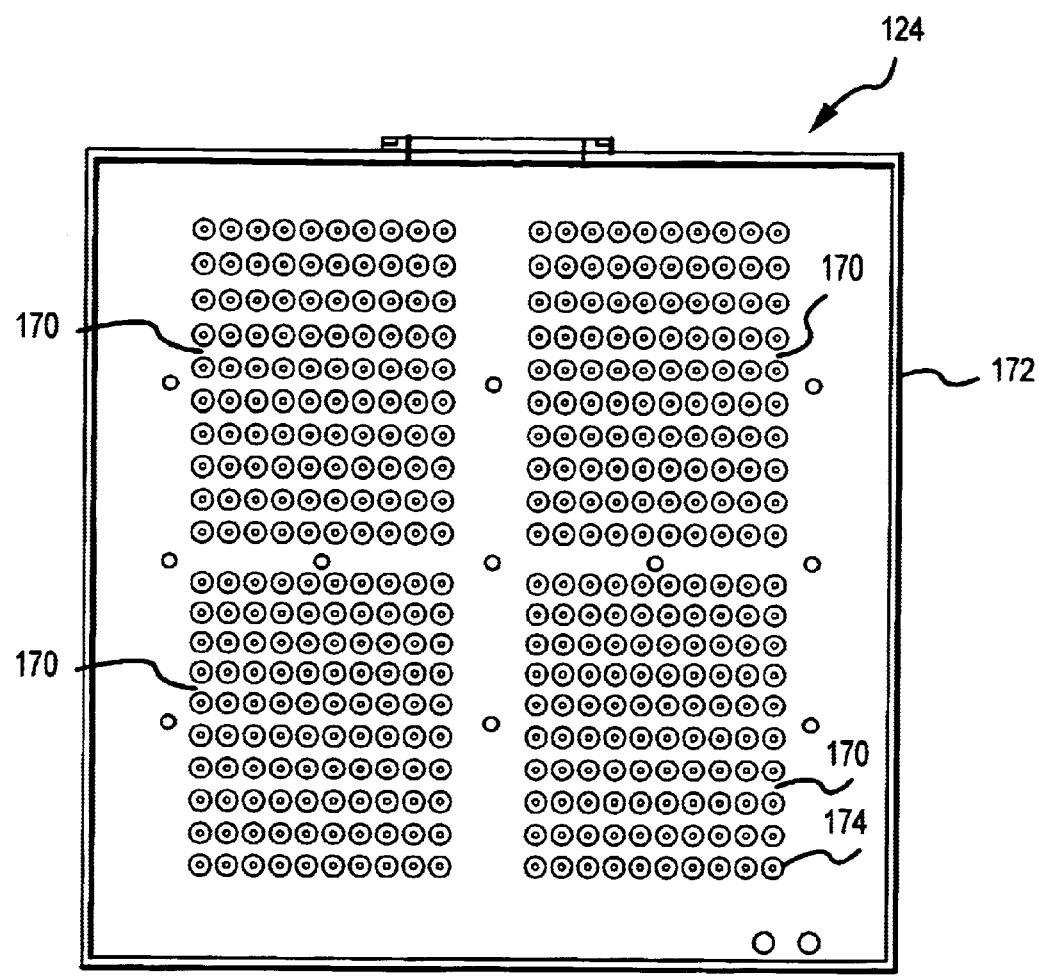
FIG. 4 is a top view of a transducer mounting plate for a 400 transducer array for use in an ultrasonic generator of the present invention.
Figure 5:
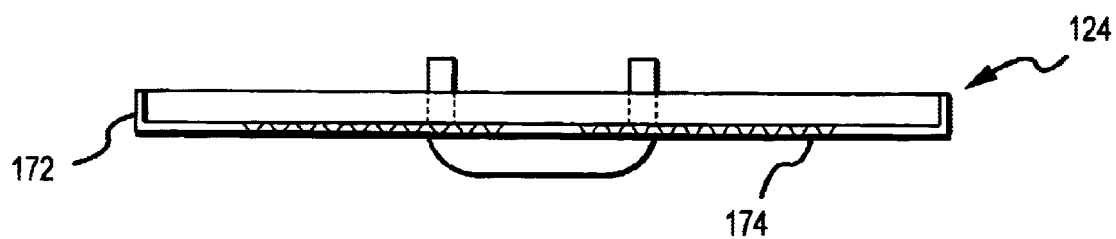
FIG. 5 is a side view of the transducer mounting plate shown in FIG. 4.

FIGS. 4–21 show component designs for an aerosol generator 106 including an array of 400 ultrasonic transducers. Referring first to FIGS. 4 and 5, the transducer mounting plate 124 is shown with a design to accommodate an array of 400 ultrasonic transducers, arranged in four subarrays of 100 ultrasonic transducers each. The transducer mounting plate 124 has integral vertical walls 172 for containing the ultrasonically transmissive fluid, typically water, in a water bath similar to the water bath volume 156 described previously with reference to FIG. 2.

Figure 6:
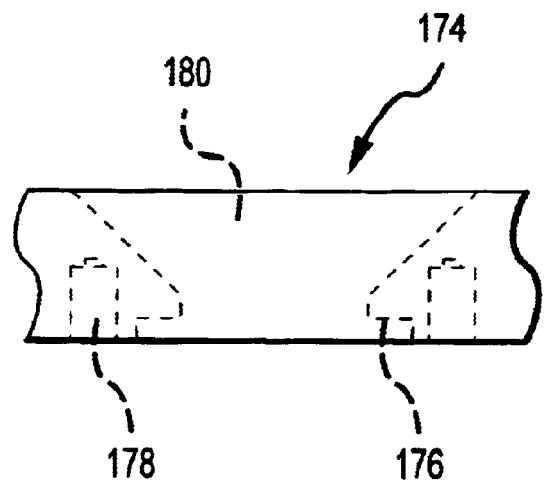
FIG. 6 is a partial side view showing the profile of a single transducer mounting receptacle of the transducer mounting plate shown in FIG. 4.

As shown in FIGS. 4 and 5, four hundred transducer mounting receptacles 174 are provided in the transducer mounting plate 124 for mounting ultrasonic transducers for the desired array. With reference to FIG. 6, the profile of an individual transducer mounting receptacle 174 is shown. A mounting seat 176 accepts an ultrasonic transducer for mounting, with a mounted ultrasonic transducer being held in place via screw holes 178. Opposite the mounting receptacle 176 is a flared opening 180 through which an ultrasonic signal may be transmitted for the purpose of generating the aerosol 108, as previously described with reference to FIG. 2.

Figure 7:
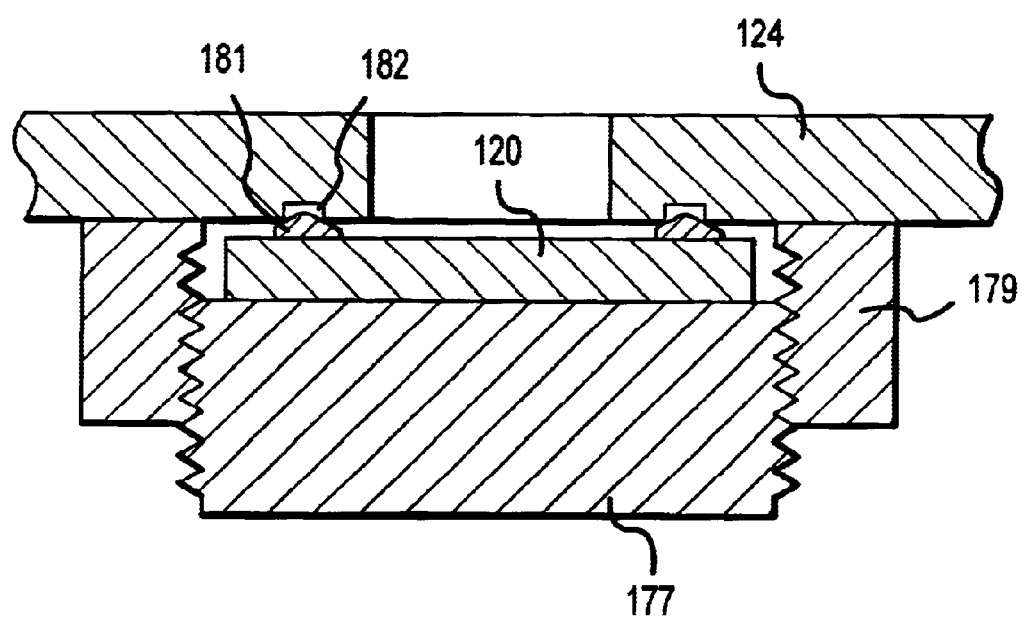
FIG. 7 is a partial side view in cross-section showing an alternative embodiment for mounting an ultrasonic transducer.

A preferred transducer mounting configuration, however, is shown in FIG. 7 for another configuration for the transducer mounting plate 124. As illustrated in FIG. 7, an ultrasonic transducer disc 120 is mounted to the transducer mounting plate 124 by use of a compression screw 177 threaded into a threaded receptacle 179. The compression screw 177 bears against the ultrasonic transducer disc 120, causing an o-ring 181, situated in an o-ring seat 182 on the transducer mounting plate, to be compressed to form a seal between the transducer mounting plate 124 and the ultrasonic transducer disc 120. This type of transducer mounting is particularly preferred when the ultrasonic transducer disc 120 includes a protective surface coating, as discussed previously, because the seal of the o-ring to the ultrasonic transducer disc 120 will be inside of the outer edge of the protective seal, thereby preventing liquid from penetrating under the protective surface coating from the edges of the ultrasonic transducer disc 120.

Figure 8:
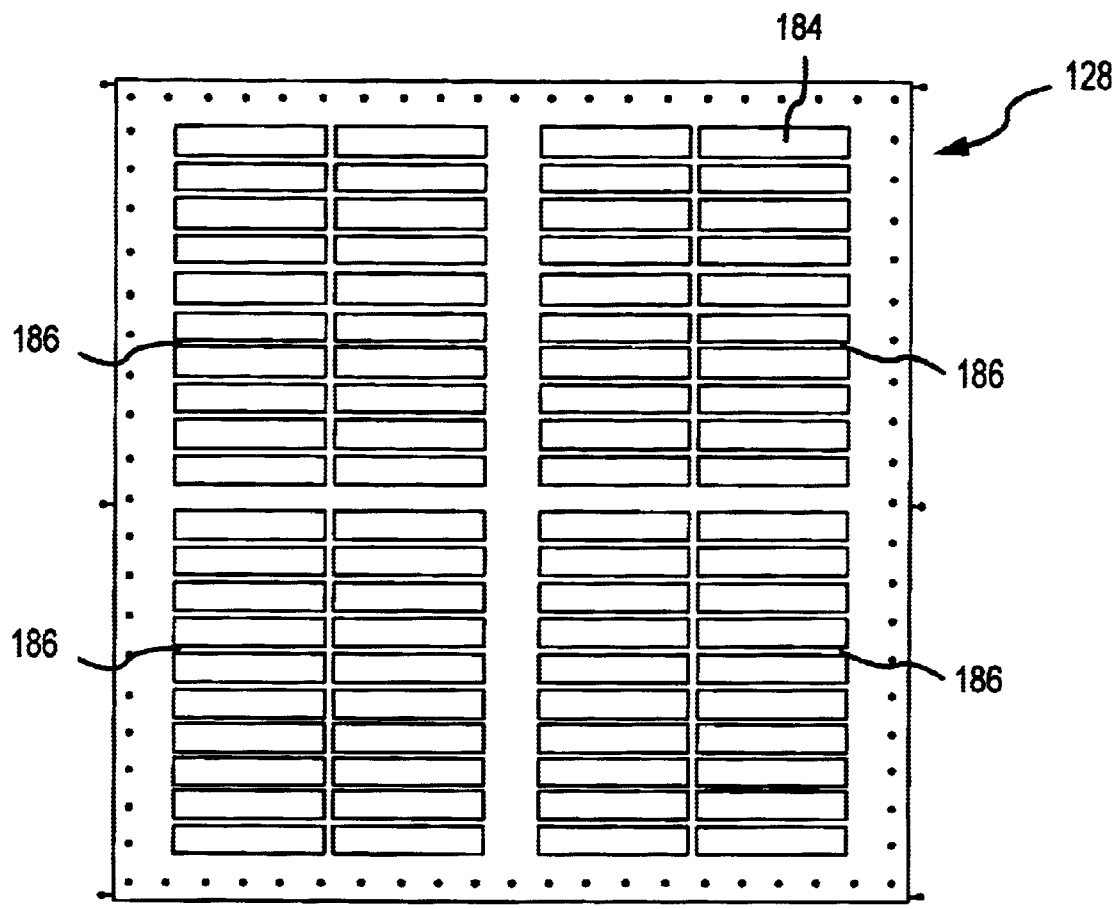
FIG. 8 is a top view of a bottom retaining plate for retaining a separator for use in an aerosol generator of the present invention.

Referring now to FIG. 8, the bottom retaining plate 128 for a 400 transducer array is shown having a design for mating with the transducer mounting plate 124 (shown in FIGS. 4–5). The bottom retaining plate 128 has eighty openings 184, arranged in four subgroups 186 of twenty openings 184 each. Each of the openings 184 corresponds with five of the transducer mounting receptacles 174 (shown in FIGS. 4–5) when the bottom retaining plate 128 is mated with the transducer mounting plate 124 to create a volume for a water bath between the transducer mounting plate 124 and the bottom retaining plate 128. The openings 184, therefore, provide a pathway for ultrasonic signals generated by ultrasonic transducers to be transmitted through the bottom retaining plate.

Figure 9:
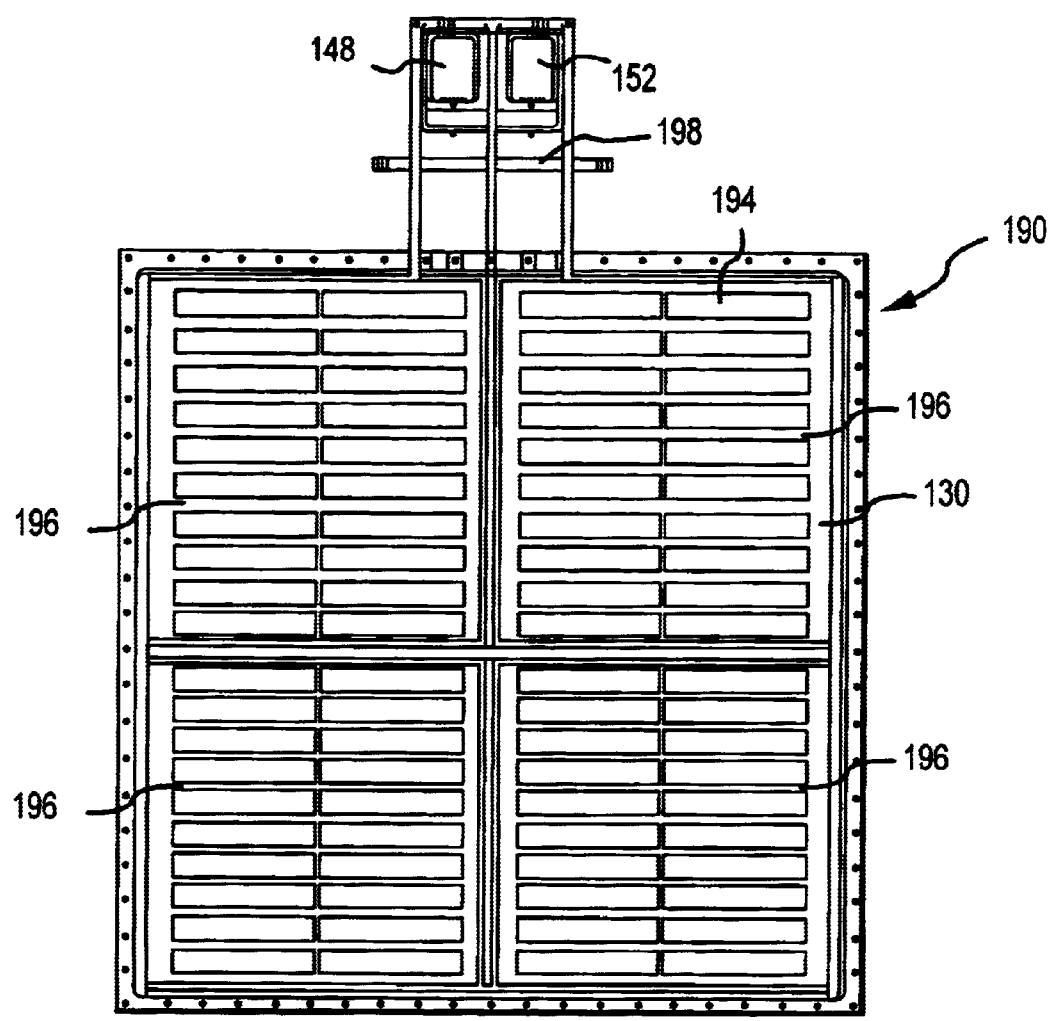
FIG. 9 is a top view of a liquid feed box having a bottom retaining plate to assist in retaining a separator for use in an aerosol generator of the present invention.
Figure 10:
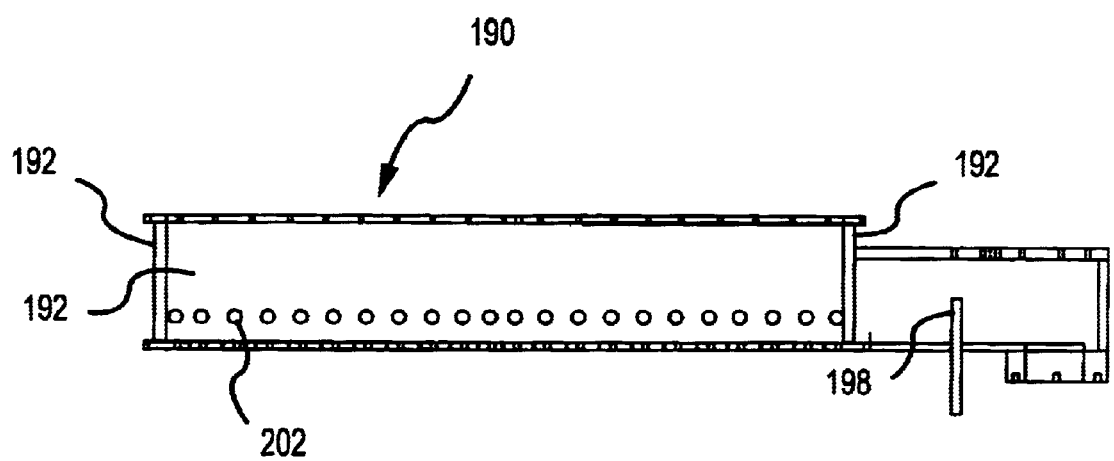
FIG. 10 is a side view of the liquid feed box shown in FIG. 9.

Referring now to FIGS. 9 and 10, a liquid feed box 190 for a 400 transducer array is shown having the top retaining plate 130 designed to fit over the bottom retaining plate 128 (shown in FIG. 8), with a separator 126 (not shown) being retained between the bottom retaining plate 128 and the top retaining plate 130 when the aerosol generator 106 is assembled. The liquid feed box 190 also includes vertically extending walls 192 for containing the liquid feed 102 when the aerosol generator is in operation. Also shown in FIGS. 9 and 10 is the feed inlet 148 and the feed outlet 152. An adjustable weir 198 determines the level of liquid feed 102 in the liquid feed box 190 during operation of the aerosol generator 106.

The top retaining plate 130 of the liquid feed box 190 has eighty openings 194 therethrough, which are arranged in four subgroups 196 of twenty openings 194 each. The openings 194 of the top retaining plate 130 correspond in size with the openings 184 of the bottom retaining plate 128 (shown in FIG. 8). When the aerosol generator 106 is assembled, the openings 194 through the top retaining plate 130 and the openings 184 through the bottom retaining plate 128 are aligned, with the separator 126 positioned therebetween, to permit transmission of ultrasonic signals when the aerosol generator 106 is in operation.

Figure 11:
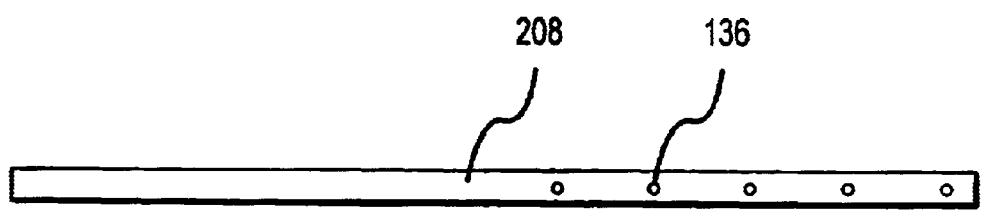
FIG. 11 is a side view of a gas tube for delivering gas within an aerosol generator of the present invention.

Referring now to FIGS. 9–11, a plurality of gas tube feed-through holes 202 extend through the vertically extending walls 192 to either side of the assembly including the feed inlet 148 and feed outlet 152 of the liquid feed box 190. The gas tube feed-through holes 202 are designed to permit insertion therethrough of gas tubes 208 of a design as shown in FIG. 11. When the aerosol generator 106 is assembled, a gas tube 208 is inserted through each of the gas tube feed-through holes 202 so that gas delivery ports 136 in the gas tube 208 will be properly positioned and aligned adjacent the openings 194 in the top retaining plate 130 for delivery of gas to atomization cones that develop in the liquid feed box 190 during operation of the aerosol generator 106. The gas delivery ports 136 are typically holes having a diameter of from about 1.5 millimeters to about 3.5 millimeters.

Figure 12:
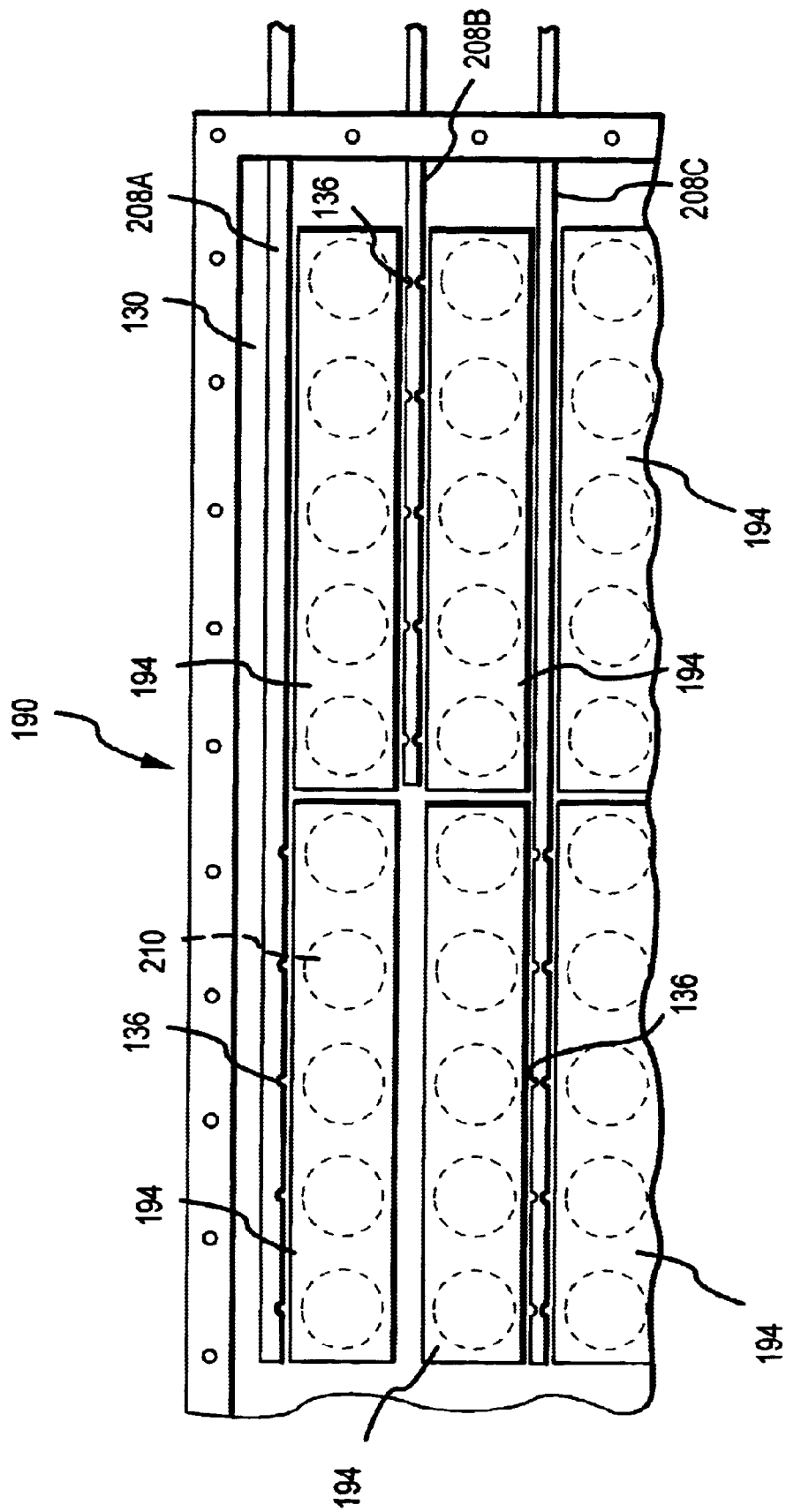
FIG. 12 shows a partial top view of gas tubes positioned in a liquid feed box for distributing gas relative to ultrasonic transducer positions for use in an aerosol generator of the present invention.

Referring now to FIG. 12, a partial view of the liquid feed box 190 is shown with gas tubes 208A, 208B and 208C positioned adjacent to the openings 194 through the top retaining plate 130. Also shown in FIG. 12 are the relative locations that ultrasonic transducer discs 120 would occupy when the aerosol generator 106 is assembled. As seen in FIG. 12, the gas tube 208A, which is at the edge of the array, has five gas delivery ports 136. Each of the gas delivery ports 136 is positioned to divert carrier gas 104 to a different one of atomization cones that develop over the array of ultrasonic transducer discs 120 when the aerosol generator 106 is operating. The gas tube 208B, which is one row in from the edge of the array, is a shorter tube that has ten gas delivery ports 136, five each on opposing sides of the gas tube 208B. The gas tube 208B, therefore, has gas delivery ports 136 for delivering gas to atomization cones corresponding with each of ten ultrasonic transducer discs 120. The third gas tube, 208C, is a longer tube that also has ten gas delivery ports 136 for delivering gas to atomization cones corresponding with ten ultrasonic transducer discs 120. The design shown in FIG. 12, therefore, includes one gas delivery port per ultrasonic transducer disc 120. Although this is a lower density of gas delivery ports 136 than for the embodiment of the aerosol generator 106 shown in FIG. 2, which includes two gas delivery ports per ultrasonic transducer disc 120, the design shown in FIG. 12 is, nevertheless, capable of producing a dense, high-quality aerosol without unnecessary waste of gas.

Figure 13:
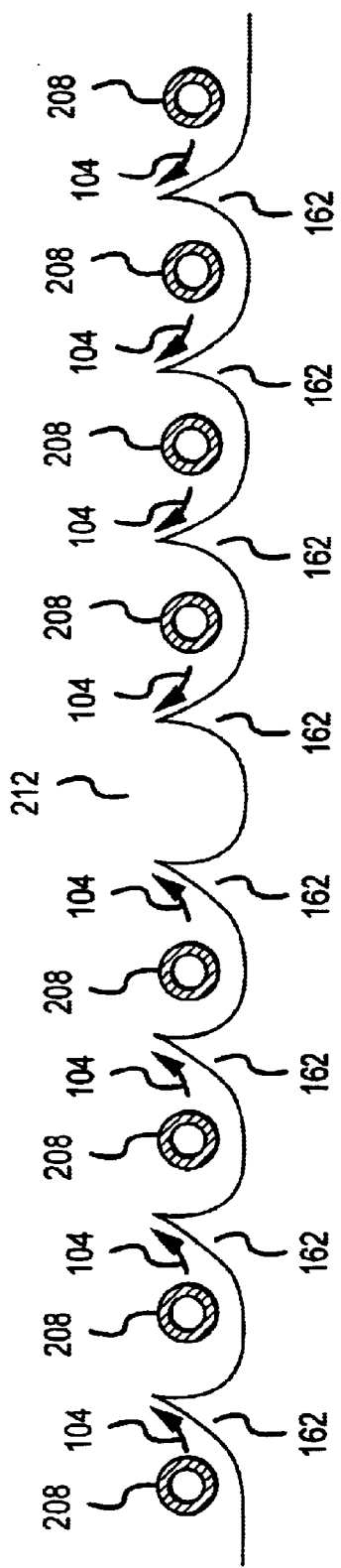
FIG. 13 shows one embodiment for a gas distribution configuration for the aerosol generator of the present invention.

Referring now to FIG. 13, the flow of carrier gas 104 relative to atomization cones 162 during operation of the aerosol generator 106 having a gas distribution configuration to deliver carrier gas 104 from gas delivery ports on both sides of the gas tubes 208, as was shown for the gas tubes 208A, 208B and 208C in the gas distribution configuration shown in FIG. 11. The carrier gas 104 sweeps both directions from each of the gas tubes 208.

Figure 14:
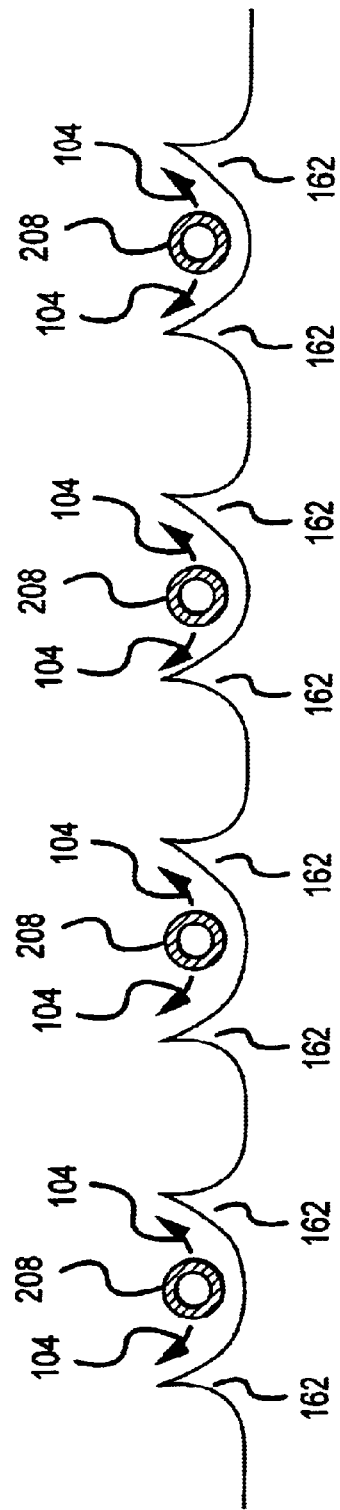
FIG. 14 shows another embodiment for a gas distribution configuration for the aerosol generator of the present invention.

An alternative, and preferred, flow for carrier gas 104 is shown in FIG. 14. As shown in FIG. 14, carrier gas 104 is delivered from only one side of each of the gas tubes 208. This results in a sweep of carrier gas from all of the gas tubes 208 toward a central area 212. This results in a more uniform flow pattern for aerosol generation that may significantly enhance the efficiency with which the carrier gas 104 is used to produce an aerosol. The aerosol that is generated, therefore, tends to be more heavily loaded with liquid droplets.

Figure 15:
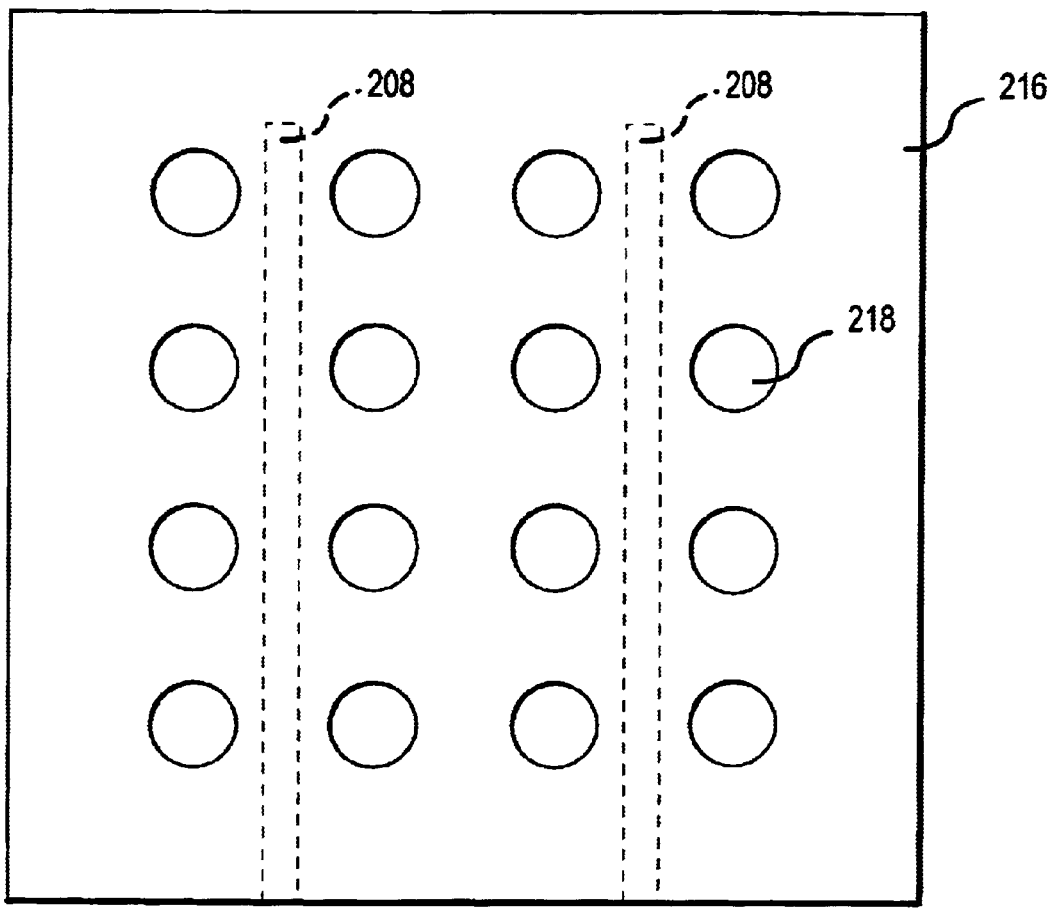
FIG. 15 is a top view of one embodiment of a gas distribution plate/gas tube assembly of the aerosol generator of the present invention.
Figure 16:
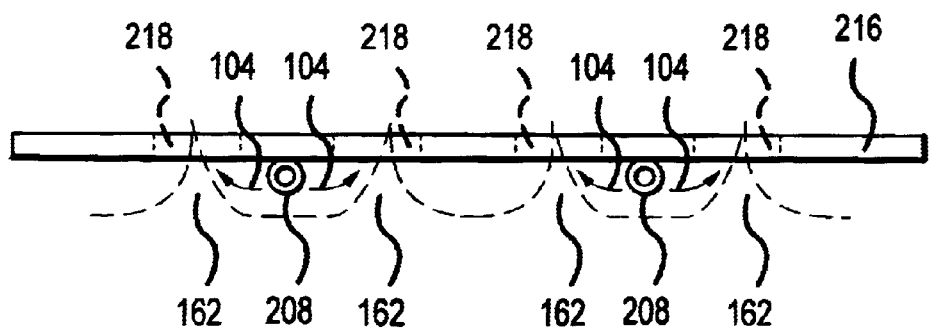
FIG. 16 is a side view of one embodiment of the gas distribution plate/gas tube assembly shown in FIG. 15.

Another configuration for distributing carrier gas in the aerosol generator 106 is shown in FIGS. 15 and 16. In this configuration, the gas tubes 208 are hung from a gas distribution plate 216 adjacent gas flow holes 218 through the gas distribution plate 216. In the aerosol generator 106, the gas distribution plate 216 would be mounted above the liquid feed, with the gas flow holes positioned to each correspond with an underlying ultrasonic transducer. Referring specifically to FIG. 16, when the ultrasonic generator 106 is in operation, atomization cones 162 develop through the gas flow holes 218, and the gas tubes 208 are located such that carrier gas 104 exiting from ports in the gas tubes 208 impinge on the atomization cones and flow upward through the gas flow holes. The gas flow holes 218, therefore, act to assist in efficiently distributing the carrier gas 104 about the atomization cones 162 for aerosol formation. It should be appreciated that the gas distribution plates 218 can be made to accommodate any number of the gas tubes 208 and gas flow holes 218. For convenience of illustration, the embodiment shown in FIGS. 15 and 16 shows a design having only two of the gas tubes 208 and only 16 of the gas flow holes 218. Also, it should be appreciated that the gas distribution plate 216 could be used alone, without the gas tubes 208. In that case, a slight positive pressure of carrier gas 104 would be maintained under the gas distribution plate 216 and the gas flow holes 218 would be sized to maintain the proper velocity of carrier gas 104 through the gas flow holes 218 for efficient aerosol generation. Because of the relative complexity of operating in that mode, however, it is not preferred.

Figure 17:
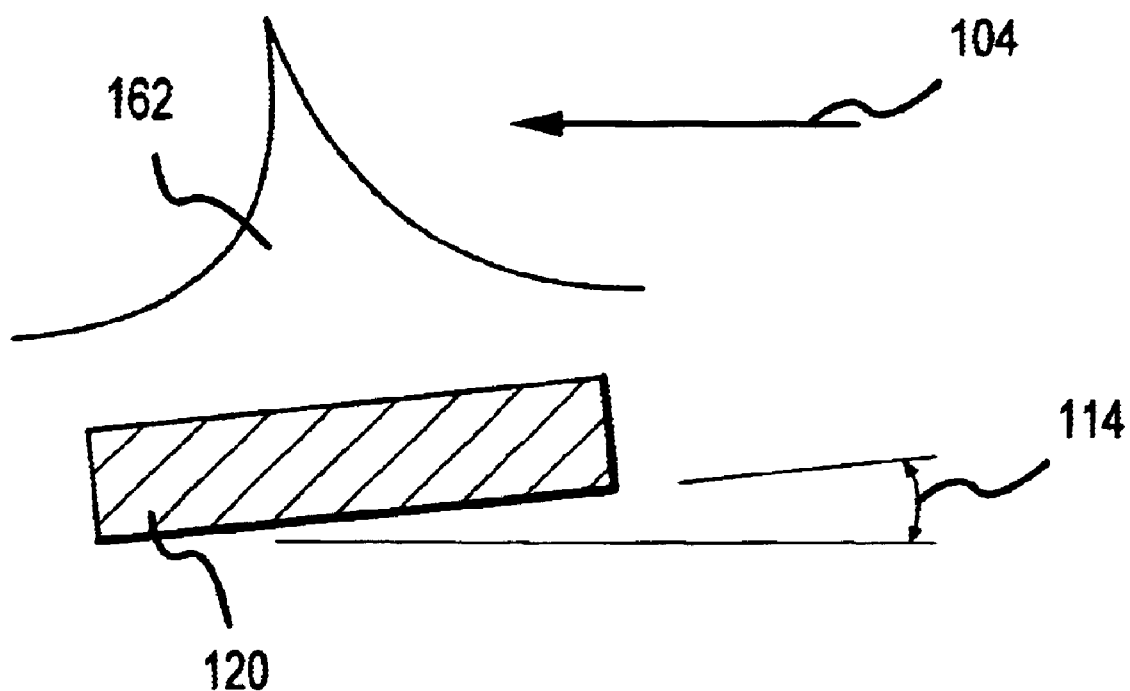
FIG. 17 shows one embodiment for orienting a transducer in the aerosol generator of the present invention.

Aerosol generation may also be enhanced through mounting of ultrasonic transducers at a slight angle and directing the carrier gas at resulting atomization cones such that the atomization cones are tilting in the same direction as the direction of flow of carrier gas. Referring to FIG. 17, an ultrasonic transducer disc 120 is shown. The ultrasonic transducer disc 120 is tilted at a tilt angle 114 (typically less than 10 degrees), so that the atomization cone 162 will also have a tilt. It is preferred that the direction of flow of the carrier gas 104 directed at the atomization cone 162 is in the same direction as the tilt of the atomization cone 162.

Figure 18:
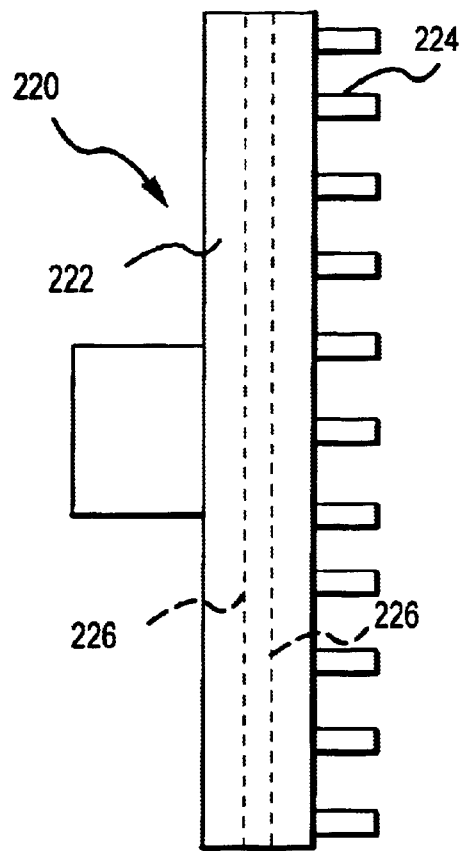
FIG. 18 is a top view of a gas manifold for distributing gas within an aerosol generator of the present invention.
Figure 19:
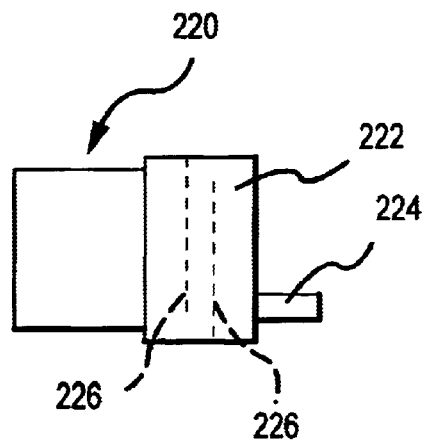
FIG. 19 is a side view of the gas manifold shown in FIG. 18.

Referring now to FIGS. 18 and 19, a gas manifold 220 is shown for distributing gas to the gas tubes 208 in a 400 transducer array design. The gas manifold 220 includes a gas distribution box 222 and piping stubs 224 for connection with gas tubes 208 (shown in FIG. 11). Inside the gas distribution box 222 are two gas distribution plates 226 that form a flow path to assist in distributing the gas equally throughout the gas distribution box 222, to promote substantially equal delivery of gas through the piping stubs 224. The gas manifold 220, as shown in FIGS. 18 and 19, is designed to feed eleven gas tubes 208. For the 400 transducer design, a total of four gas manifolds 220 are required.

Figure 20:
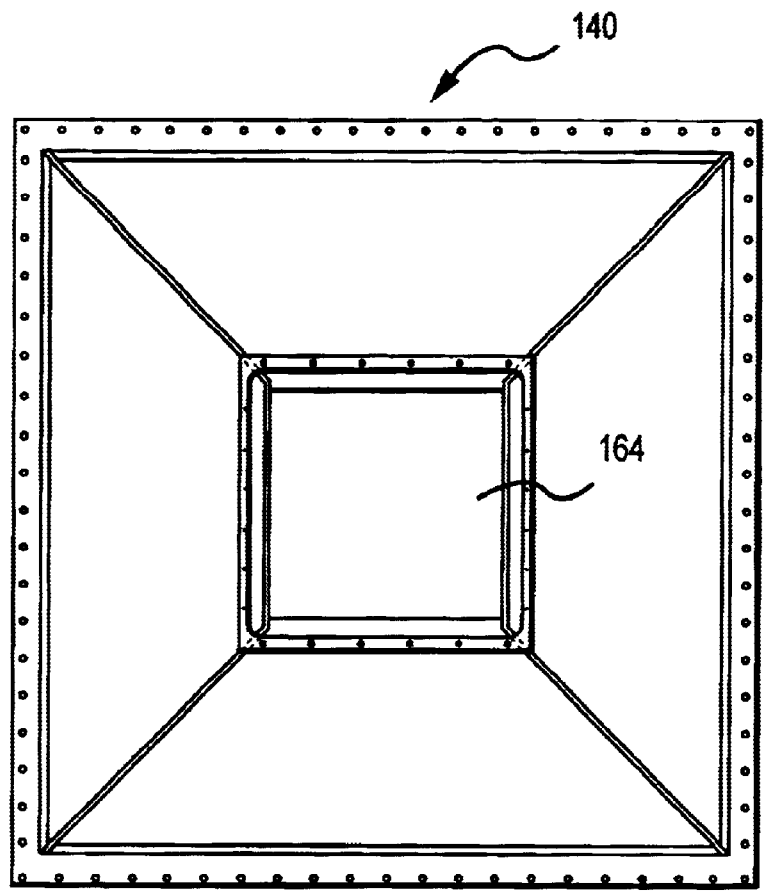
FIG. 20 is a top view of a generator lid of a hood design for use in an aerosol generator of the present invention.
Figure 21:
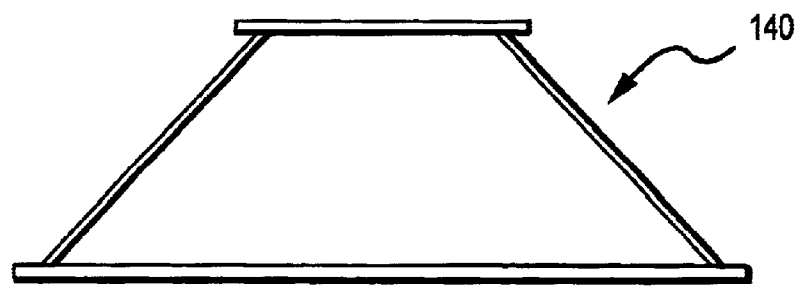
FIG. 21 is a side view of the generator lid shown in FIG. 20.
Figure 22:
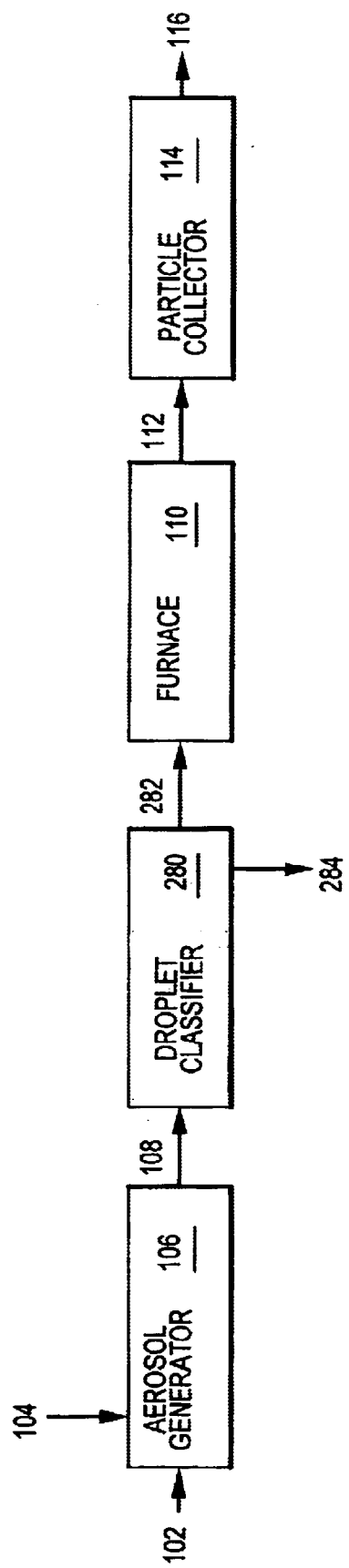
FIG. 22 is a process block diagram of one embodiment of the process of the present invention including a droplet classifier.
Figure 23:
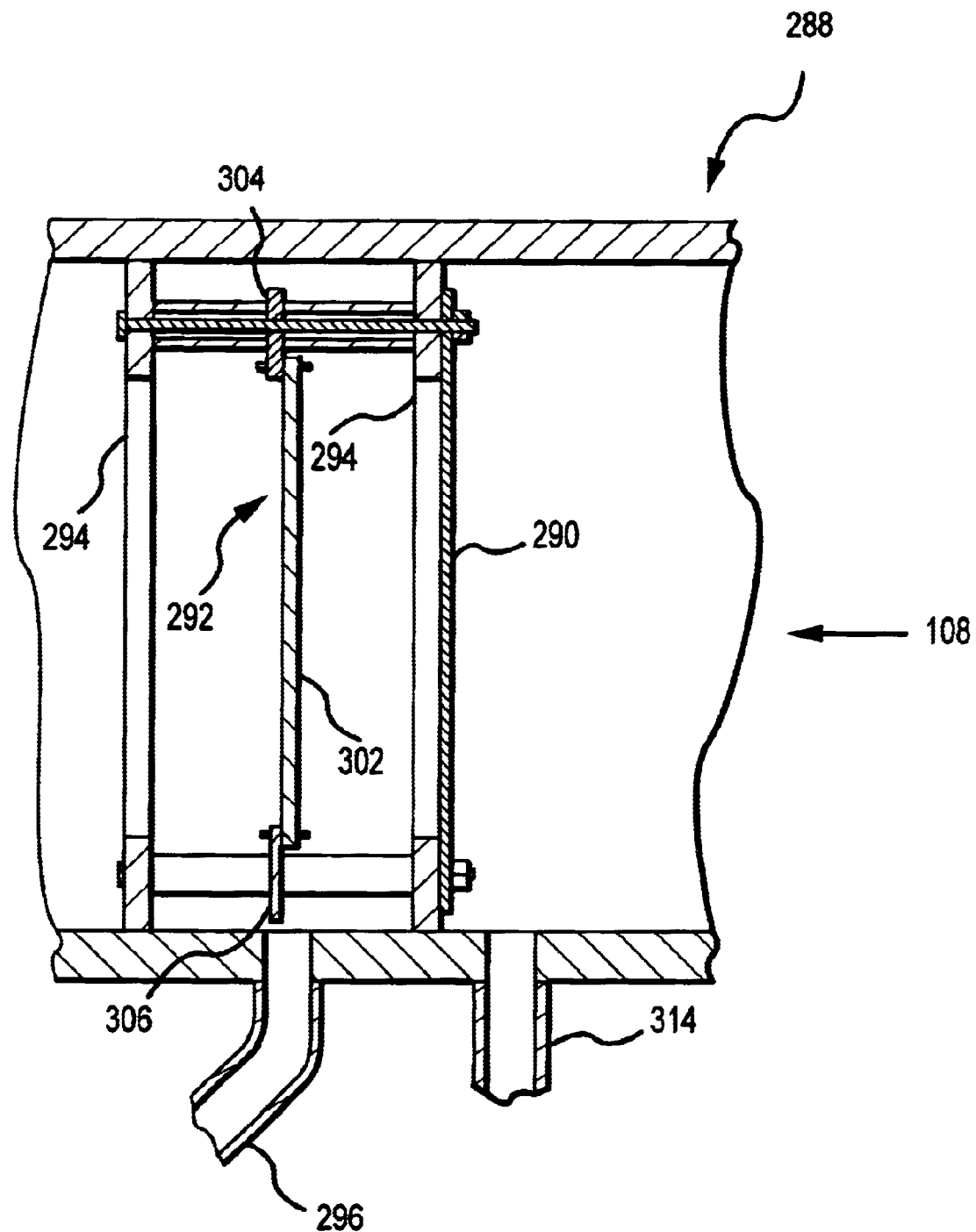
FIG. 23 is a top view in cross section of an impactor of the present invention for use in classifying an aerosol.
Figure 24:
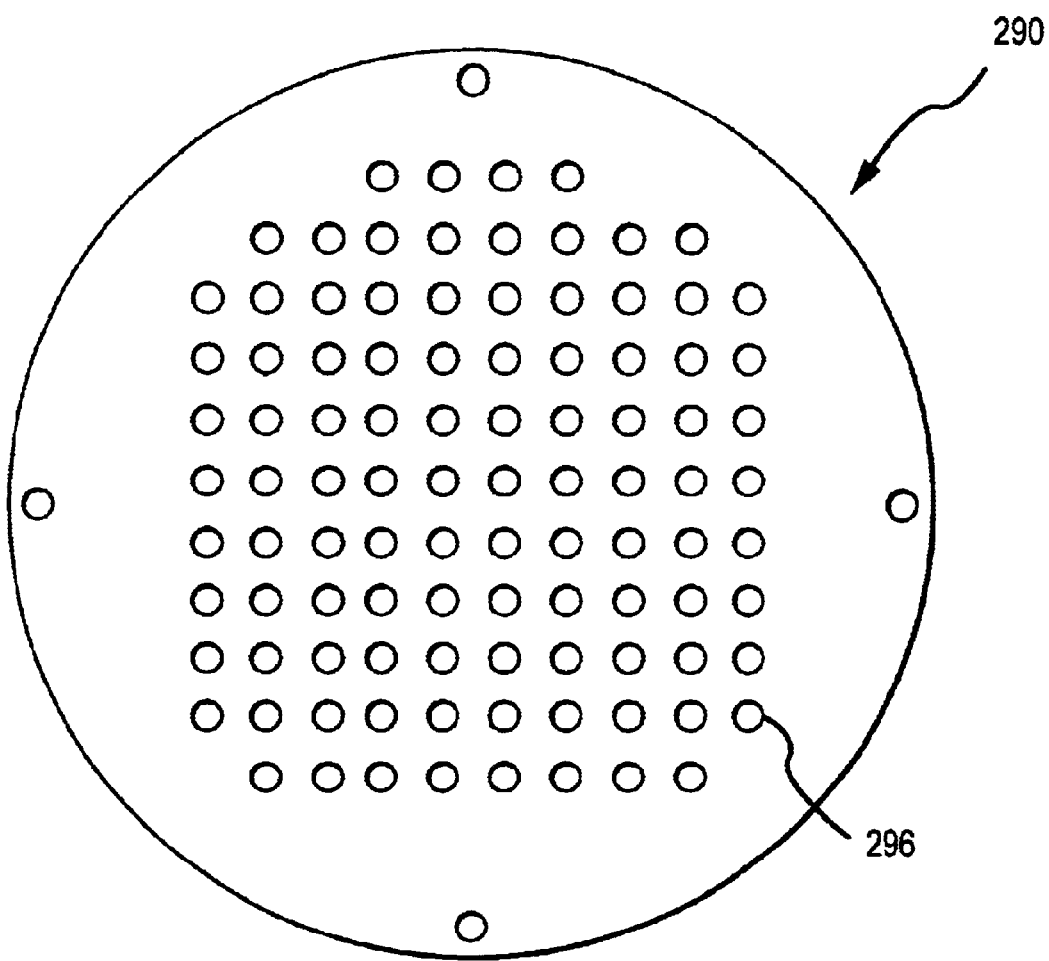
FIG. 24 is a front view of a flow control plate of the impactor shown in FIG. 23.
Figure 25:
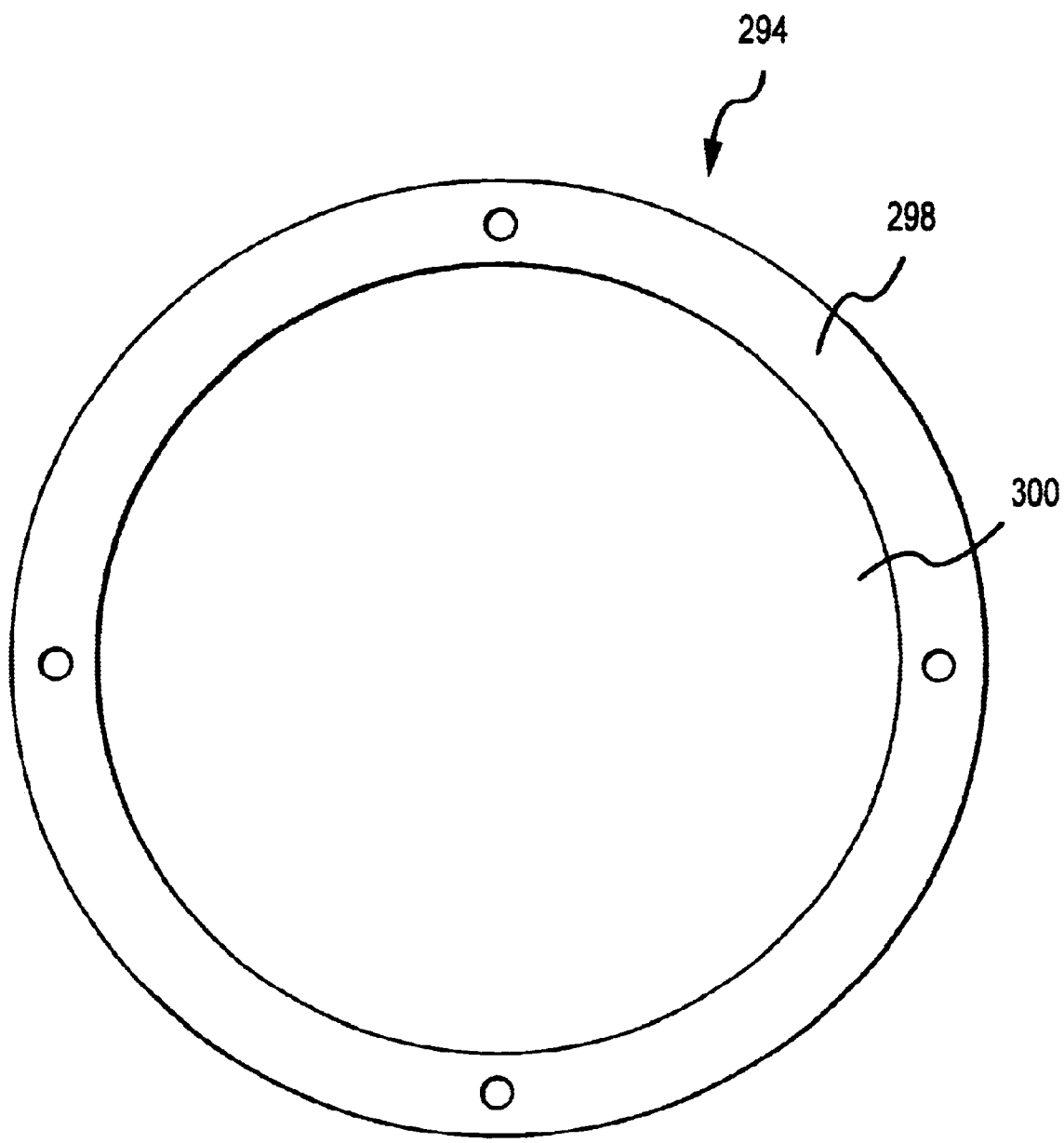
FIG. 25 is a front view of a mounting plate of the impactor shown in FIG. 23.
Figure 26:
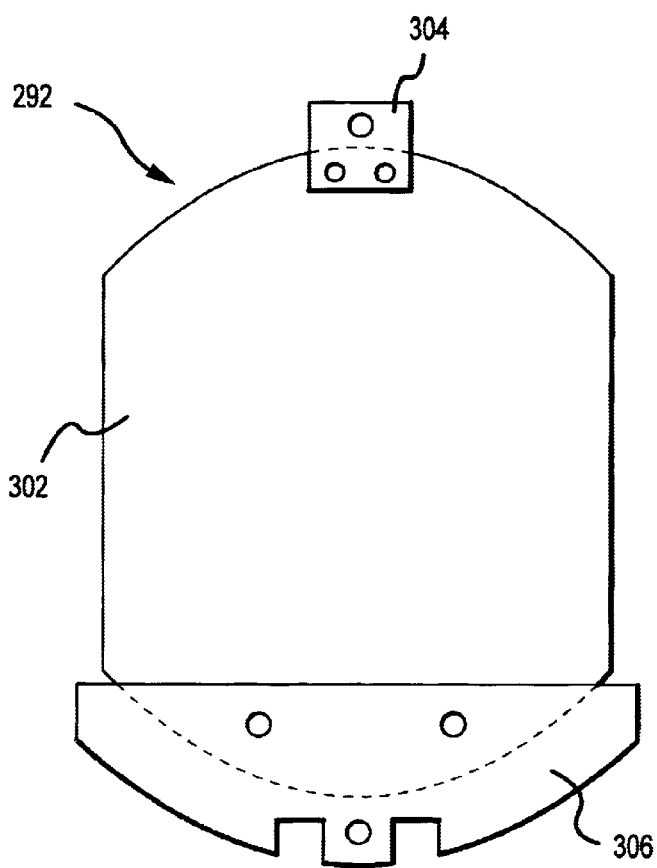
FIG. 26 is a front view of an impactor plate assembly of the impactor shown in FIG. 23.
Figure 27:
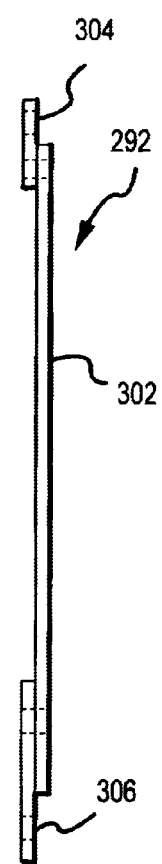
FIG. 27 is a side view of the impactor plate assembly shown in FIG. 26.
Figure 28:
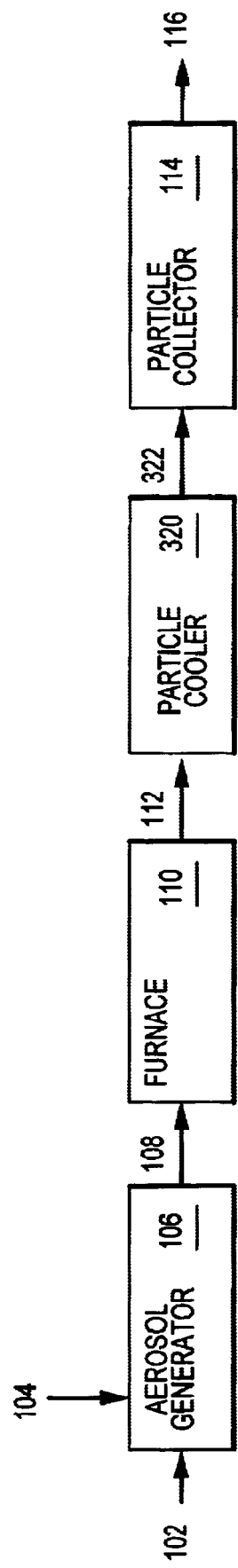
FIG. 28 is a process block diagram of one embodiment of the present invention including a particle cooler.

Referring now to FIGS. 20 and 21, the generator lid 140 is shown for a 400 transducer array design. The generator lid 140 mates with and covers the liquid feed box 190 (shown in FIGS. 9 and 10). The generator lid 140, as shown in FIGS. 20 and 21, has a hood design to permit easy collection of the aerosol 108 without subjecting droplets in the aerosol 108 to sharp edges on which droplets may coalesce and be lost, and possibly interfere with the proper operation of the aerosol generator 106. When the aerosol generator 106 is in operation, the aerosol 108 would be withdrawn via the aerosol exit opening 164 through the generator cover 140.

It is important that the aerosol stream that is fed to the furnace 110 have a high droplet flow rate and high droplet loading as would be required for most industrial applications. With the present invention, the aerosol stream fed to the furnace preferably includes a droplet flow of greater than about 0.5 liters per hour, more preferably greater than about 2 liters per hour, still more preferably greater than about 5 liters per hour, even more preferably greater than about 10 liters per hour, particularly greater than about 50 liters per hour and most preferably greater than about 100 liters per hour; and with the droplet loading being typically greater than about 0.04 milliliters of droplets per liter of carrier gas, preferably greater than about 0.083 milliliters of droplets per liter of carrier gas 104, more preferably greater than about 0.167 milliliters of droplets per liter of carrier gas 104, still more preferably greater than about 0.25 milliliters of droplets per liter of carrier gas 104, particularly greater than about 0.33 milliliters of droplets per liter of carrier gas 104 104.

As discussed previously, the aerosol generator 106 of the present invention produces a concentrated, high quality aerosol of micro-sized droplets having a relatively narrow size distribution. However, the process of the present invention can be enhanced by further classifying by size the droplets in the aerosol 108 prior to introduction of the droplets into the furnace 110. In this manner, the size and size distribution of particles in the particulate product 116 are further controlled.

Referring now to FIG. 22, a process flow diagram is shown for one embodiment of the process of the present invention including such droplet classification. As shown in FIG. 22, the aerosol 108 from the aerosol generator 106 goes to a droplet classifier 280 where oversized droplets are removed from the aerosol 108 to prepare a classified aerosol 282. Liquid 284 from the oversized droplets that are being removed is drained from the droplet classifier 280. This drained liquid 284 may advantageously be recycled for use in preparing additional liquid feed 102.

Any suitable droplet classifier may be used for removing droplets above a predetermined size. For example, a cyclone could be used to remove over-size droplets.

A preferred droplet classifier for many applications, however, is an impactor. One embodiment of an impactor for use with the present invention will now be described with reference to FIGS. 23–27.

As seen in FIG. 23, an impactor 288 has disposed in a flow conduit 286 a flow control plate 290 and an impactor plate assembly 292. The flow control plate 290 is conveniently mounted on a mounting plate 294.

The flow control plate 290 is used to channel the flow of the aerosol stream toward the impactor plate assembly 292 in a manner with controlled flow characteristics that are desirable for proper impaction of oversize droplets on the impactor plate assembly 292 for removal through the drains 296 and 314. One embodiment of the flow control plate 290 is shown in FIG. 24. The flow control plate 290 has an array of circular flow ports 296 for channeling flow of the aerosol 108 towards the impactor plate assembly 292 with the desired flow characteristics.

Details of the mounting plate 294 are shown in FIG. 25. The mounting plate 294 has a mounting flange 298 with a large diameter flow opening 300 passing therethrough to permit access of the aerosol 108 to the flow ports 296 of the flow control plate 290 (shown in FIG. 24).

Referring now to FIGS. 26 and 27, one embodiment of an impactor plate assembly 292 is shown. The impactor plate assembly 292 includes an impactor plate 302 and mounting brackets 304 and 306 used to mount the impactor plate 302 inside of the flow conduit 286. The impactor plate 302 and the flow channel plate 290 are designed so that droplets larger than a predetermined size will have momentum that is too large for those particles to change flow direction to navigate around the impactor plate 302.

During operation of the impactor 288, the aerosol 108 from the aerosol generator 106 passes through the upstream flow control plate 290. Most of the droplets in the aerosol navigate around the impactor plate 302 and exit the impactor 288 through the downstream flow control plate 290 in the classified aerosol 282. Droplets in the aerosol 108 that are too large to navigate around the impactor plate 302 will impact on the impactor plate 302 and drain through the drain 296 to be collected with the drained liquid 284 (as shown in FIG. 23).

The configuration of the impactor plate 302 shown in FIG. 22 represents only one of many possible configurations for the impactor plate 302. For example, the impactor 288 could include an upstream flow control plate 290 having vertically extending flow slits therethrough that are offset from vertically extending flow slits through the impactor plate 302, such that droplets too large to navigate the change in flow due to the offset of the flow slits between the flow control plate 290 and the impactor plate 302 would impact on the impactor plate 302 to be drained away. Other designs are also possible.

In a preferred embodiment of the present invention, the droplet classifier 280 is typically designed to remove droplets from the aerosol 108 that are larger than about 15 $\mu$m, more preferably to remove droplets larger than about 10 $\mu$m, even more preferably to remove droplets of a size larger than about 7 $\mu$m. Depending upon the specific application, however, the droplet classification size may be varied, such as by changing the spacing between the impactor plate 302 and the flow control plate 290 or increasing or decreasing aerosol velocity through the jets in the flow control plate 290 by varying jet diameter, for example. Because the aerosol generator 106 of the present invention initially produces a high quality aerosol 108, having a relatively narrow size distribution of droplets, typically less than about 30 weight percent of liquid feed 102 in the aerosol 108 is removed as the drain liquid 284 in the droplet classifier 288, with preferably less than about 35 weight percent being removed, even more preferably less than about 30 weight percent being removed and most preferably less than about 20 weight percent being removed. Minimizing the removal of liquid feed 102 from the aerosol 108 is particularly important for commercial applications to increase the yield of high quality particulate product 116. The impactor can also advantageously reduce the build-up of larger droplets that can deposit by various mechanisms such as gravitational settling.

With some applications of the process of the present invention, it may be possible to collect the glass particles 112 directly from the output of the furnace 110. More often, however, it will be desirable to cool the glass particles 112 exiting the furnace 110 prior to collection of the particles 112 in the particle collector 114. Referring now to FIG. 28, one embodiment of the process of the present invention is shown in which the particles 112 exiting the furnace 110 are sent to a particle cooler 320 to produce a cooled particle stream 322, which is then fed to the particle collector 114. Although the particle cooler 320 may be any cooling apparatus capable of cooling the particles 112 to the desired temperature for introduction into the particle collector 114, traditional heat exchanger designs are not preferred. This is because a traditional heat exchanger design ordinarily directly subjects the aerosol stream, in which the hot particles 112 are suspended, to cool surfaces. In that situation, significant losses of the particles 112 occur due to thermophoretic deposition of the hot particles 112 on the cool surfaces of the heat exchanger. According to the present invention, a gas quench apparatus is provided for use as the particle cooler 320 that significantly reduces thermophoretic losses compared to a traditional heat exchanger.

Figure 29:
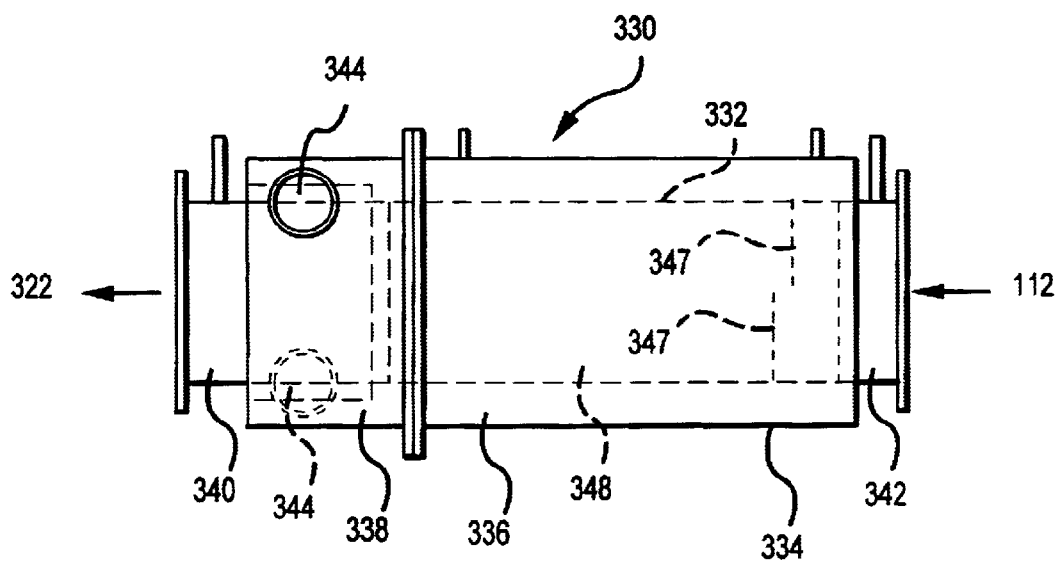
FIG. 29 is a top view of a gas quench cooler of the present invention.
Figures 30, 31:
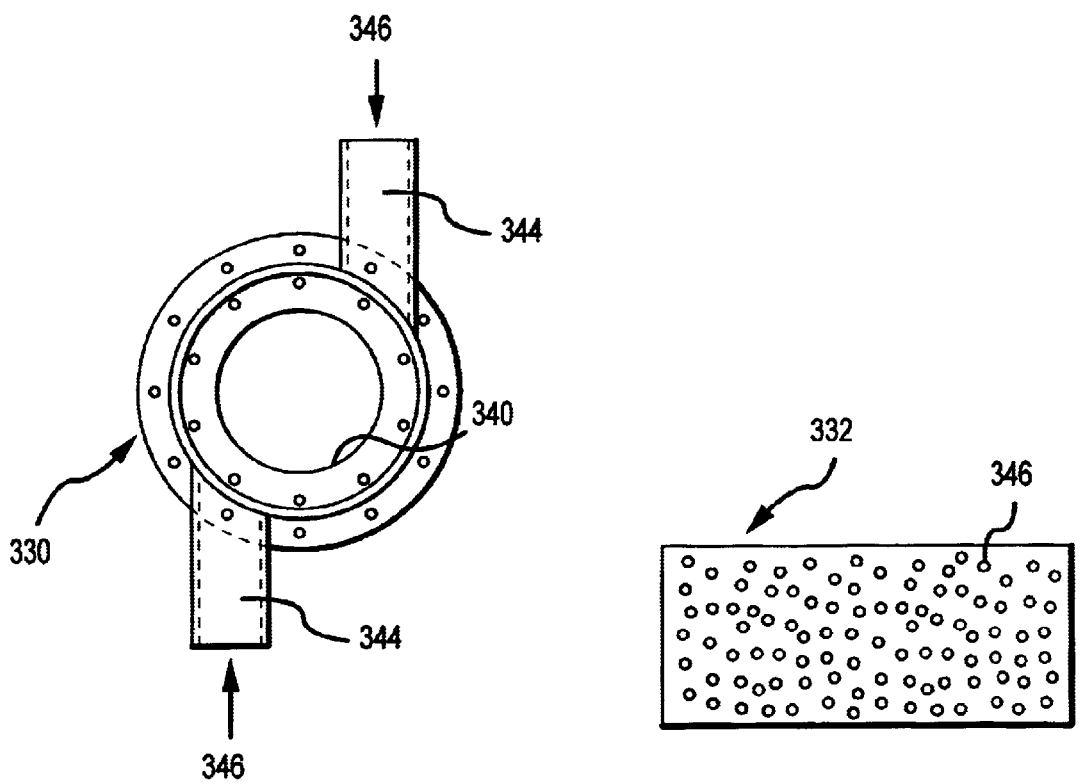
FIG. 30 is an end view of the gas quench cooler shown in FIG. 29.
FIG. 31 is a side view of a perforated conduit of the quench cooler shown in FIG. 29.
Figure 32:
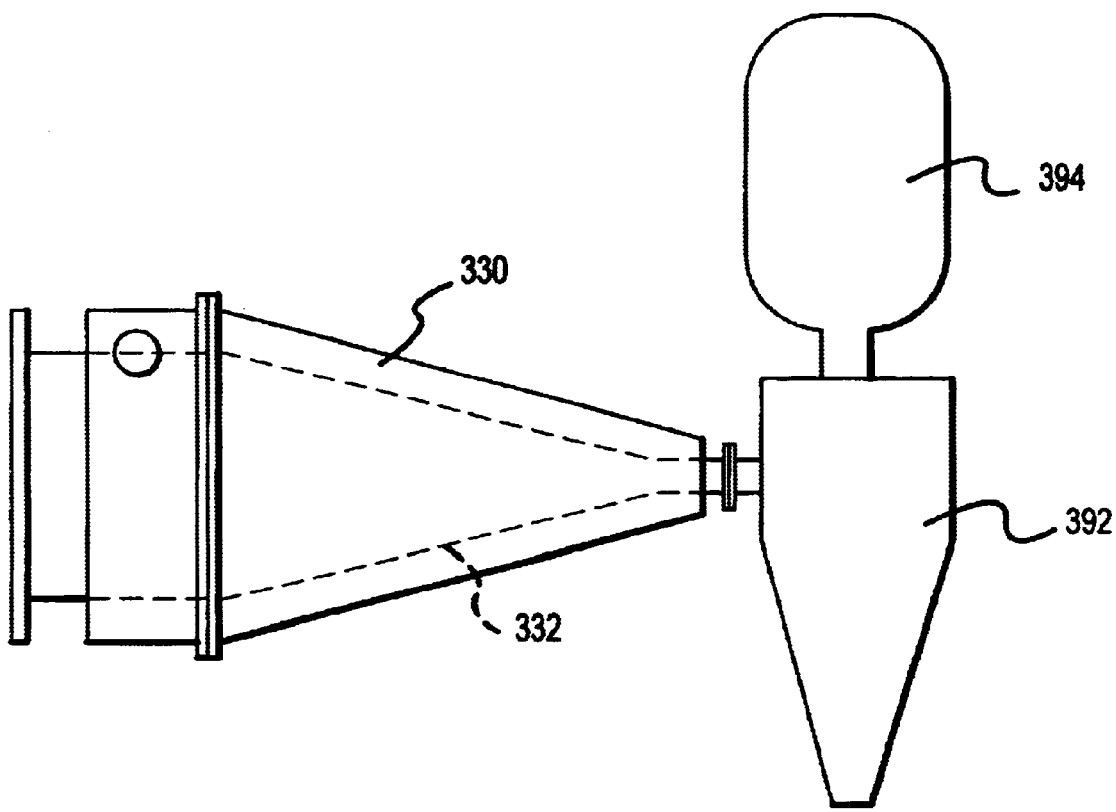
FIG. 32 is a side view showing one embodiment of a gas quench cooler of the present invention connected with a cyclone.

Referring now to FIGS. 29–31, one embodiment of a gas quench cooler 330 is shown. The gas quench cooler includes a perforated conduit 332 housed inside of a cooler housing 334 with an annular space 336 located between the cooler housing 334 and the perforated conduit 332. In fluid communication with the annular space 336 is a quench gas inlet box 338, inside of which is disposed a portion of an aerosol outlet conduit 340. The perforated conduit 332 extends between the aerosol outlet conduit 340 and an aerosol inlet conduit 342. Attached to an opening into the quench gas inlet box 338 are two quench gas feed tubes 344. Referring specifically to FIG. 31, the perforated tube 332 is shown. The perforated tube 332 has a plurality of openings 345. The openings 345, when the perforated conduit 332 is assembled into the gas quench cooler 330, permit the flow of quench gas 346 from the annular space 336 into the interior space 348 of the perforated conduit 332. Although the openings 345 are shown as being round holes, any shape of opening could be used, such as slits. Also, the perforated conduit 332 could be a porous screen. Two heat radiation shields 347 prevent downstream radiant heating from the furnace. In most instances, however, it will not be necessary to include the heat radiation shields 347, because downstream radiant heating from the furnace is normally not a significant problem. Use of the heat radiation shields 347 is not preferred due to particulate losses that accompany their use.

Figure 33:
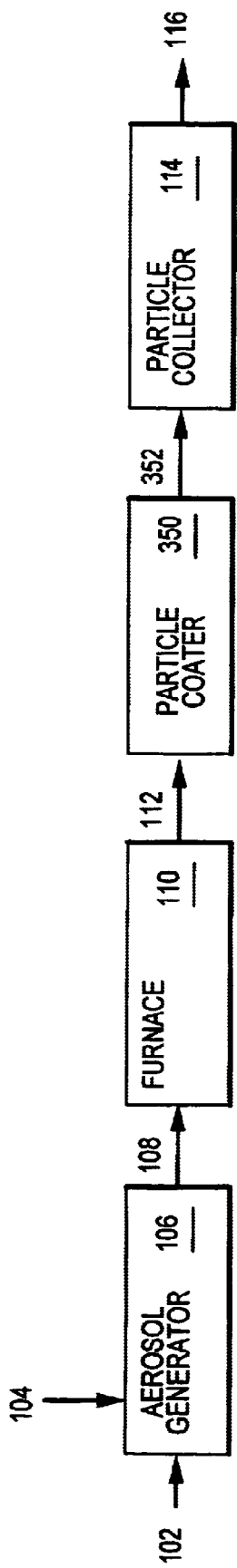
FIG. 33 is a process block diagram of one embodiment of the present invention including a particle coater.
Figure 34:
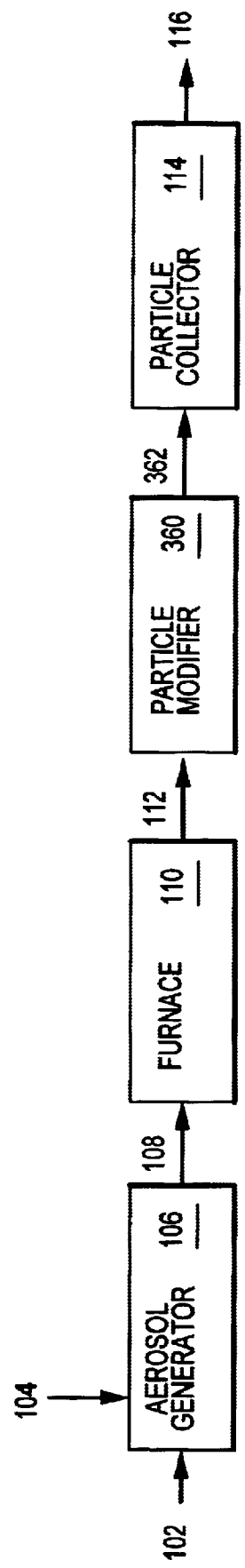
FIG. 34 is a block diagram of one embodiment of the present invention including a particle modifier.

With continued reference to FIGS. 29–31, operation of the gas quench cooler 330 will now be described. During operation, the particles 112, carried by and dispersed in a gas stream, enter the gas quench cooler 330 through the aerosol inlet conduit 342 and flow into the interior space 348 of perforated conduit 332. Quench gas 346 is introduced through the quench gas feed tubes 344 into the quench gas inlet box 338. Quench gas 346 entering the quench gas inlet box 338 encounters the outer surface of the aerosol outlet conduit 340, forcing the quench gas 346 to flow, in a spiraling, swirling manner, into the annular space 336, where the quench gas 346 flows through the openings 345 through the walls of the perforated conduit 332. Preferably, the gas 346 retains some swirling motion even after passing into the interior space 348. In this way, the particles 112 are quickly cooled with low losses of particles to the walls of the gas quench cooler 330. In this manner, the quench gas 346 enters in a radial direction into the interior space 348 of the perforated conduit 332 around the entire periphery, or circumference, of the perforated conduit 332 and over the entire length of the perforated conduit 332. The cool quench gas 346 mixes with and cools the hot particles 112, which then exit through the aerosol outlet conduit 340 as the cooled particle stream 322. The cooled particle stream 322 can then be sent to the particle collector 114 for particle collection. The temperature of the cooled particle stream 322 is controlled by introducing more or less quench gas. Also, as shown in FIG. 29, the quench gas 346 is fed into the quench cooler 330 in counter flow to flow of the particles. Alternatively, the quench cooler could be designed so that the quench gas 346 is fed into the quench cooler in concurrent flow with the flow of the particles 112. The amount of quench gas 346 fed to the gas quench cooler 330 will depend upon the specific material being made and the specific operating conditions. The quantity of quench gas 346 used, however, must be sufficient to reduce the temperature of the aerosol steam including the particles 112 to the desired temperature. Typically, the particles 112 are cooled to a temperature at least below about 200° C., and often lower. The only limitation on how much the particles 112 are cooled is that the cooled particle stream 322 must be at a temperature that is above the condensation temperature for water as another condensable vapor in the stream. The temperature of the cooled particle stream 322 is often at a temperature of from about 50° C. to about 120° C.

Because of the entry of quench gas 346 into the interior space 348 of the perforated conduit 322 in a radial direction about the entire circumference and length of the perforated conduit 322, a buffer of the cool quench gas 346 is formed about the inner wall of the perforated conduit 332, thereby significantly inhibiting the loss of hot particles 112 due to thermophoretic deposition on the cool wall of the perforated conduit 332. In operation, the quench gas 346 exiting the openings 345 and entering into the interior space 348 should have a radial velocity (velocity inward toward the center of the circular cross-section of the perforated conduit 332) of larger than the thermophoretic velocity of the particles 112 inside the perforated conduit 332 in a direction radially outward toward the perforated wall of the perforated conduit 332.

As seen in FIGS. 29–31, the gas quench cooler 330 includes a flow path for the particles 112 through the gas quench cooler of a substantially constant cross-sectional shape and area. Preferably, the flow path through the gas quench cooler 330 will have the same cross-sectional shape and area as the flow path through the furnace 110 and through the conduit delivering the aerosol 108 from the aerosol generator 106 to the furnace 110. In one embodiment, however, it may be necessary to reduce the cross-sectional area available for flow prior to the particle collector 114. This is the case, for example, when the particle collector includes a cyclone for separating particles in the cooled particle stream 322 from gas in the cooled particle stream 322. This is because of the high inlet velocity requirements into cyclone separators.

Referring now to FIG. 32, one embodiment of the gas quench cooler 330 is shown in combination with a cyclone separator 392. The perforated conduit 332 has a continuously decreasing cross-sectional area for flow to increase the velocity of flow to the proper value for the feed to cyclone separator 392. Attached to the cyclone separator 392 is a bag filter 394 for final clean-up of overflow from the cyclone separator 392. Separated particles exit with underflow from the cyclone separator 392 and may be collected in any convenient container. The use of cyclone separation is particularly preferred for glass powder batches having a weight average size of larger than about 1 μm, although a series of cyclones may be needed to obtain the desired degree of separation. Cyclone separation is particularly preferred for powders having a weight average size of larger than about 1.5 μm.

In an additional embodiment, the process of the present invention can also incorporate compositional modification of the glass particles 112 exiting the furnace. Most commonly, the compositional modification will involve forming on the glass particles 112 a material phase that is different than that of the particles 112, such as by coating the glass particles 112 with a coating material. One embodiment of the process of the present invention incorporating particle coating is shown in FIG. 33. As shown in FIG. 33, the glass particles 112 exiting from the furnace 110 go to a particle coater 350 where a coating is placed over the outer surface of the glass particles 112 to form coated particles 352, which are then sent to the particle collector 114 for preparation of the particulate product 116. Coating methodologies employed in the particle coater 350 are discussed in more detail below.

With continued reference primarily to FIG. 33, in a preferred embodiment, when the particles 112 are coated according to the process of the present invention, the particles 112 are also manufactured via the aerosol process of the present invention, as previously described. The process of the present invention can, however, be used to coat particles that have been premanufactured by a different process. When coating particles that have been premanufactured by a different route, such as by liquid precipitation, it is preferred that the particles remain in a dispersed state from the time of manufacture to the time that the particles are introduced in slurry form into the aerosol generator 106 for preparation of the aerosol 108 to form the dry particles 112 in the furnace 110, which particles 112 can then be coated in the particle coater 350. Maintaining particles in a dispersed state from manufacture through coating avoids problems associated with agglomeration and redispersion of particles if particles must be redispersed in the liquid feed 102 for feed to the aerosol generator 106. For example, for particles originally precipitated from a liquid medium, the liquid medium containing the suspended precipitated glass particles could be used to form the liquid feed 102 to the aerosol generator 106. It should be noted that the particle coater 350 could be an integral extension of the furnace 110 or could be a separate piece of equipment.

The quench gas can also contain a high degree of moisture that can assist in hydroxylation of the glass particle surface. The particles of the present invention can also be etched in the gas phase prior to collection. The purpose of etching the particles is to increase the surface area of the particle that is available for surface modification, such as silanation, and to increase the surface area available for bonding when used in a resin.

In a further embodiment of the present invention, following preparation of the particles 112 in the furnace 110, the particles 112 may then be structurally modified to impart desired physical properties prior to particle collection. Referring now to FIG. 34, one embodiment of the process of the present invention is shown including such structural particle modification. The particles 112 exiting the furnace 110 go to a particle modifier 360 where the particles are structurally modified to form modified particles 362, which are then sent to the particle collector 114 for preparation of the particulate product 116. The particle modifier 360 is typically a furnace, such as an annealing furnace, which may be integral with the furnace 110 or may be a separate heating device. Regardless, it is important that the particle modifier 360 have temperature control that is independent of the furnace 110, so that the proper conditions for particle modification may be provided separate from conditions required of the furnace 110 to prepare the glass particles 112. The particle modifier 360, therefore, typically provides a temperature controlled environment and necessary residence time to effect the desired structural modification of the particles 112.

The structural modification that occurs in the particle modifier 360 may be any modification to the structure or morphology of the glass particles 112. For example, the particles 112 may be annealed in the particle modifier 360 to densify the glass particles 112 or to partially recrystallize the glass particles 112 into a polycrystalline form.

Aerosol generation with the process of the present invention has thus far been described with respect to the ultrasonic aerosol generator. Use of the ultrasonic generator is preferred for the process of the present invention because of the extremely high quality and dense aerosol generated. In some instances, however, the aerosol generation for the process of the present invention may have a different design depending upon the specific application. For example, when larger particles are desired, such as those having a weight average size of larger than about 3 μm, a spray nozzle atomizer may be preferred. For smaller-particle applications, however, and particularly for those applications to produce particles smaller than about 3 μm, as is generally desired with the particles of the present invention, an ultrasonic generator, as described herein, is particularly preferred. In that regard, the ultrasonic generator of the present invention is particularly preferred for when making particles with a weight average size of from about 0.1 μm to about 3 μm.

Although ultrasonic aerosol generators have been used for medical applications and home humidifiers, use of ultrasonic generators for spray pyrolysis particle manufacture has largely been confined to small-scale, experimental situations. The ultrasonic aerosol generator of the present invention described with reference to FIGS. 2–21, however, is well suited for commercial production of high quality powders with a small average size and a narrow size distribution. In that regard, the aerosol generator produces a high quality aerosol, with heavy droplet loading and at a high rate of production. Such a combination of small droplet size, narrow size distribution, heavy droplet loading, and high production rate provide significant advantages over existing aerosol generators that usually suffer from at least one of inadequately narrow size distribution, undesirably low droplet loading, or unacceptably low production rate.

Through the careful and controlled design of the ultrasonic generator of the present invention, an aerosol may be produced typically having greater than about 70 weight percent (and preferably greater than about 80 weight percent) of droplets in the size range of from about 1 μm to about 15 μm, preferably in a size range of from about 1 μm to about 10 μm and more preferably from about 2 μm to about 4 μm. Also, the ultrasonic generator of the present invention is capable of delivering high output rates of liquid feed in the aerosol. The rate of liquid feed, at the high liquid loadings previously described, is preferably greater than about 20 milliliters per hour per transducer, more preferably greater than about 30 milliliters per hour per transducer and even more preferably greater than about 50 milliliters per hour per transducer. This high level of performance is desirable for commercial operations and is accomplished with the present invention with a relatively simple design including a single precursor bath over an array of ultrasonic transducers. The ultrasonic generator is made for high aerosol production rates at a high droplet loading, and with a narrow size distribution of droplets. The generator preferably produces an aerosol at a rate of greater than about 0.5 liter per hour of droplets, more preferably greater than about 2 liters per hour of droplets, still more preferably greater than about 5 liters per hour of droplets, even more preferably greater than about 10 liters per hour of droplets and most preferably greater than about 40 liters per hour of droplets. For example, when the aerosol generator has a 400 transducer design, as described with reference to FIGS. 4–21, the aerosol generator is capable of producing a high quality aerosol having high droplet loading as previously described, at a total production rate of preferably greater than about 10 liters per hour of liquid feed, more preferably greater than about 15 liters per hour of liquid feed, even more preferably greater than about 20 liters per hour of liquid feed and most preferably greater than about 40 liters per hour of liquid feed.

Under most operating conditions, when using such an aerosol generator, total particulate product produced is preferably greater than about 0.5 gram per hour per transducer, more preferably greater than about 0.75 gram per hour per transducer, even more preferably greater than about 1.0 gram per hour per transducer and most preferably greater than about 2.0 grams per hour per transducer.

One significant aspect of the process of the present invention for manufacturing particulate materials is the unique flow characteristics encountered in the furnace relative to laboratory scale systems. The maximum Reynolds number attained for flow in the furnace 110 with the present invention is very high, typically in excess of 500, preferably in excess of 1,000 and more preferably in excess of 2,000. In most instances, however, the maximum Reynolds number for flow in the furnace will not exceed 10,000, preferably will not exceed 5,000 and most preferably will not exceed 3,000. This is significantly different from lab-scale systems where the Reynolds number for flow in a reactor is typically lower than 300 and rarely exceeds 200.

The Reynolds number is a dimensionless quantity characterizing flow of a fluid which, for flow through a circular cross sectional conduit is defined as:

$$Re = \frac{\rho v d}{\mu}$$

where: $\rho$ = fluid density;
$v$ = fluid mean velocity;
$d$ = conduit inside diameter; and
$\mu$ = fluid viscosity.

It should be noted that the values for density, velocity and viscosity will vary along the length of the furnace 110.

One problem with operating under flow conditions at a high Reynolds number is that undesirable volatilization of components is much more likely to occur than in systems having flow characteristics as found in laboratory-scale systems. The volatilization problem occurs with the present invention, because the furnace is typically operated over a substantial section of the heating zone in a constant wall heat flux mode, due to limitations in heat transfer capability. This is significantly different than operation of a furnace at a laboratory scale, which typically involves operation of most of the heating zone of the furnace in a uniform wall temperature mode, because the heating load is sufficiently small that the system is not heat transfer limited.

With the present invention, it is typically preferred to heat the aerosol stream in the heating zone of the furnace as quickly as possible to the desired temperature range for particle manufacture. Because of flow characteristics in the furnace and heat transfer limitations, during rapid heating of the aerosol the wall temperature of the furnace can significantly exceed the maximum average target temperature for the stream. This is a problem because, even though the average stream temperature may be within the range desired, the wall temperature may become so hot that components in the vicinity of the wall are subjected to temperatures high enough to undesirably volatilize the components. This volatilization near the wall of the furnace can cause formation of significant quantities of ultrafine particles that are outside of the size range desired.

Therefore, with the present invention, it is preferred that when the flow characteristics in the furnace are such that the Reynolds number through any part of the furnace exceeds 500, more preferably exceeds 1,000, and most preferably exceeds 2,000, the maximum wall temperature in the furnace should be kept at a temperature that is below the temperature at which a desired component of the final particles would exert a vapor pressure not exceeding about 200 millitorr, more preferably not exceeding about 100 millitorr, and most preferably not exceeding about 50 millitorr. Furthermore, the maximum wall temperature in the furnace should also be kept below a temperature at which an intermediate component, from which a final component is to be at least partially derived, should also have a vapor pressure not exceeding the magnitudes noted for components of the final product.

In addition to maintaining the furnace wall temperature below a level that could create volatilization problems, it is also important that this not be accomplished at the expense of the desired average stream temperature. The maximum average stream temperature must be maintained at a high enough level so that the particles will have a desired high density. The maximum average stream temperature should, however, generally be a temperature at which a component in the final particles, or an intermediate component from which a component in the final particles is at least partially derived, would exert a vapor pressure not exceeding about 100 millitorr, preferably not exceeding about 50 millitorr, and most preferably not exceeding about 25 millitorr.

So long as the maximum wall temperature and the average stream temperature are kept below the point at which detrimental volatilization occurs, it is generally desirable to heat the stream as fast as possible and to remove resulting particles from the furnace immediately after the maximum stream temperature is reached in the furnace, while allowing sufficient time at the maximum temperature for the conversion to take place. With the present invention, the average residence time in the heating zone of the furnace may typically be maintained at greater than 1 second, more preferably greater than 2 seconds, even more preferably greater than 5 seconds and most preferably greater than 10 seconds.

Another significant issue with respect to operating the process of the present invention, which includes high aerosol flow rates, is loss within the system of materials intended for incorporation into the final particulate product. Material losses in the system can be quite high if the system is not properly operated. If system losses are too high, the process would not be practical for use in the manufacture of particulate products of many materials. This has typically not been a major consideration with laboratory-scale systems.

One significant potential for loss with the process of the present invention is thermophoretic losses that occur when a hot aerosol stream is in the presence of a cooler surface. In that regard, the use of the quench cooler, as previously described, with the process of the present invention provides an efficient way to cool the particles without unreasonably high thermophoretic losses. There is also, however, significant potential for losses occurring near the end of the furnace and between the furnace and the cooling unit.

It has been found that thermophoretic losses in the back end of the furnace can be significantly controlled if the heating zone of the furnace is operated such that the maximum stream temperature is not attained until near the end of the heating zone in the furnace, and at least not until the last third of the heating zone. When the heating zone includes a plurality of heating sections, the maximum average stream temperature should ordinarily not occur until at least the last heating section. Furthermore, the heating zone should typically extend to as close to the exit of the furnace as possible. This is counter to conventional thought which is to typically maintain the exit portion of the furnace at a low temperature to avoid having to seal the furnace outlet at a high temperature. Such cooling of the exit portion of the furnace, however, significantly promotes thermophoretic losses. Furthermore, the potential for operating problems that could result in thermophoretic losses at the back end of the furnace are reduced with the very short residence times in the furnace for the present invention, as discussed previously.

Typically, it would be desirable to instantaneously cool the aerosol upon exiting the furnace. This is not possible. It is possible, however, to make the residence time between the furnace outlet and the cooling unit as short as possible. Furthermore, it is desirable to insulate the aerosol conduit occurring between the furnace exit and the cooling unit entrance. Even more preferred is to insulate that conduit and, even more preferably, to also heat that conduit so that the wall temperature of that conduit is at least as high as the average stream temperature of the aerosol stream. Furthermore, it is desirable that the cooling unit operate in a manner such that the aerosol is quickly cooled in a manner to prevent thermophoretic losses during cooling. The quench cooler, described previously, is very effective for cooling with low losses. Furthermore, to keep the potential for thermophoretic losses very low, it is preferred that the residence time of the aerosol stream between attaining the maximum stream temperature in the furnace and a point at which the aerosol has been cooled to an average stream temperature below about 200° C. is shorter than about 2 seconds, more preferably shorter than about 1 second, and even more preferably shorter than about 0.5 second and most preferably shorter than about 0.1 second. In most instances, the maximum average stream temperature attained in the furnace will be greater than about 800° C. Furthermore, the total residence time from the beginning of the heating zone in the furnace to a point at which the average stream temperature is at a temperature below about 200° C. should typically be longer than about 1 seconds, preferably longer than about 2 seconds, more preferably longer than about 5 seconds, and most preferably shorter than about 10 seconds.

Another part of the process with significant potential for thermophoretic losses is after particle cooling until the particles are finally collected. Proper particle collection is very important to reducing losses within the system. The potential for thermophoretic losses is significant following particle cooling because the aerosol stream is still at an elevated temperature to prevent detrimental condensation of water in the aerosol stream. Therefore, cooler surfaces of particle collection equipment can result in significant thermophoretic losses.

To reduce the potential for thermophoretic losses before the particles are finally collected, it is important that the transition between the cooling unit and particle collection be as short as possible. Preferably, the output from the quench cooler is immediately sent to a particle separator, such as a filter unit or a cyclone. In that regard, the total residence time of the aerosol between attaining the maximum average stream temperature in the furnace and the final collection of the particles is preferably shorter than about 2 seconds, more preferably shorter than about 1 second, still more preferably shorter than about 0.5 second and most preferably shorter than about 0.1 second. Furthermore, the residence time between the beginning of the heating zone in the furnace and final collection of the particles is preferably shorter than about 6 seconds, more preferably shorter than about 3 seconds, even more preferably shorter than about 2 seconds, and most preferably shorter than about 1 second. Furthermore, the potential for thermophoretic losses may be reduced by insulating the conduit section between the cooling unit and the particle collector and, even more preferably, by also insulating around the filter, when a filter is used for particle collection. The potential for losses may be reduced even further by heating of the conduit section between the cooling unit and the particle collection equipment, so that the internal equipment surfaces are at least slightly warmer than the aerosol stream average stream temperature. Furthermore, when a filter is used for particle collection, the filter could be heated. For example, insulation could be wrapped around a filter unit, with electric heating inside of the insulating layer to maintain the walls of the filter unit at a desired elevated temperature higher than the temperature of filter elements in the filter unit, thereby reducing thermophoretic particle losses to walls of the filter unit.

Even with careful operation to reduce thermophoretic losses, some losses will still occur. For example, some particles will inevitably be lost to walls of particle collection equipment, such as the walls of a cyclone or filter housing. These surfaces can be washed with air jets to remove particles from these surfaces. One way to reduce these losses, and correspondingly increase product yield, is to periodically wash the interior of the particle collection equipment to remove particles adhering to the sides. In most cases, the wash fluid will be water, unless water would have a detrimental effect on one of the components of the particles. For example, the particle collection equipment could include parallel collection paths. One path could be used for active particle collection while the other is being washed. The wash could include an automatic or manual flush without disconnecting the equipment. Alternatively, the equipment to be washed could be disconnected to permit access to the interior of the equipment for a thorough wash. As an alternative to having parallel collection paths, the process could simply be shut down occasionally to permit disconnection of the equipment for washing. The removed equipment could be replaced with a clean piece of equipment and the process could then be resumed while the disconnected equipment is being washed.

For example, a cyclone or filter unit could periodically be disconnected and particles adhering to interior walls could be removed by a water wash. The particles could then be dried in a low temperature dryer, typically at a temperature of lower than about 50° C.

Another area for potential losses in the system, and for the occurrence of potential operating problems, is between the outlet of the aerosol generator and the inlet of the furnace. Losses here are not due to thermophoresis, but rather to liquid coming out of the aerosol and impinging and collecting on conduit and equipment surfaces. Although this loss is undesirable from a material yield standpoint, the loss may be even more detrimental to other aspects of the process. For example, water collecting on surfaces may release large droplets that can lead to large particles that detrimentally contaminate the particulate product. Furthermore, if accumulated liquid reaches the furnace, the liquid can cause excessive temperature gradients within the furnace tube, which can cause furnace tube failure, especially for ceramic tubes. One way to reduce the potential for undesirable liquid buildup in the system is to provide adequate drains. In that regard, it is preferred that a drain be placed as close as possible to the furnace inlet to prevent liquid accumulations from reaching the furnace. The drain should be placed, however, far enough in advance of the furnace inlet such that the stream temperature is lower than about 80° C. at the drain location. It has also been found that the use of an impactor at the front of the system removes larger particles that might otherwise settle out and deposit on the walls.

Another way to reduce the potential for undesirable liquid buildup is for the conduit between the aerosol generator outlet and the furnace inlet to be of a substantially constant cross-sectional area and configuration. Preferably, the conduit beginning with the aerosol generator outlet, passing through the furnace and continuing to at least the cooling unit inlet is of a substantially constant cross-sectional area and geometry.

Another way to reduce the potential for undesirable buildup is to heat at least a portion, and preferably the entire length, of the conduit between the aerosol generator and the inlet to the furnace. For example, the conduit could be wrapped with a heating tape to maintain the inside walls of the conduit at a temperature higher than the temperature of the aerosol. The aerosol would then tend to concentrate toward the center of the conduit due to thermophoresis. Fewer aerosol droplets would, therefore, be likely to impinge on conduit walls or other surfaces making the transition to the furnace.

Another way to reduce the potential for undesirable liquid buildup is to introduce a dry gas into the aerosol between the aerosol generator and the furnace. Addition of the dry gas causes vaporization of at least a part of the moisture in the aerosol, and preferably substantially all of the moisture in the aerosol, to form a dried aerosol, which is then introduced into the furnace.

The dry gas will most often be dry air, although in some instances it may be desirable to use dry nitrogen gas or some other dry gas. If sufficient a sufficient quantity of the dry gas is used, the droplets of the aerosol are substantially completely dried to beneficially form dried precursor particles in aerosol form for introduction into the furnace, where the precursor particles are then pyrolyzed to make a desired particulate product. Also, the use of the dry gas typically will reduce the potential for contact between droplets of the aerosol and the conduit wall, especially in the critical area in the vicinity of the inlet to the furnace. In that regard, a preferred method for introducing the dry gas into the aerosol is from a radial direction into the aerosol. For example, equipment of substantially the same design as the quench cooler, described previously with reference to FIGS. 29–31, could be used, with the aerosol flowing through the interior flow path of the apparatus and the dry gas being introduced through perforated wall of the perforated conduit. An alternative to using the dry gas to dry the aerosol would be to use a low temperature thermal preheater/dryer prior to the furnace to dry the aerosol prior to introduction into the furnace. This alternative is not, however, preferred.

Still another way to reduce the potential for losses due to liquid accumulation is to operate the process with equipment configurations such that the aerosol stream flows in a vertical direction from the aerosol generator to and through the furnace. For smaller-size particles, those smaller than about 1.5 μm, this vertical flow should, preferably, be vertically upward. For larger-size particles, such as those larger than about 1.5 μm, the vertical flow is preferably vertically downward.

Furthermore, with the process of the present invention, the potential for system losses is significantly reduced because the total system retention time from the outlet of the generator until collection of the particles is preferably shorter than about 15 seconds, more preferably shorter than about 10 seconds, even more preferably shorter than about 7 seconds and most preferably shorter than about 5 seconds.

Thus, it is an advantage of the present invention that the product yield is extremely high based on the amount of glass precursors in the liquid. Accordingly, it is preferred that at least about 95 weight percent, more preferably at least about 98 weight percent of the glass precursors in the liquid feed 102 are converted to the glass particles.

To form substantially uniform coatings on the surface of the glass particles, if desired, a reactive gas composition can be contacted with the glass particles at an elevated temperature after the particles have been formed. For example, the reactive gas can be introduced into the heated reaction zone at the distal end so that the desired compound deposits on the surface of the particles.

More specifically, the droplets can enter the heated reaction zone at a first end such that the droplets move through the heating zone and form the glass particles. At the opposite end of the heating zone, a reactive gas composition can be introduced such that the reactive gas composition contacts the glass particles at an elevated temperature. Alternatively, the reactive gas composition can be contacted with the heated particles in a separate heating zone located downstream from the heated reaction zone.

Coatings can be generated on the particle surface by a number of different mechanisms. One or more precursors can vaporize and fuse to the hot particle surface and thermally react resulting in the formation of a thin-film coating by chemical vapor deposition (CVD). Preferred coatings deposited by CVD include elemental metals. Further, the coating can be formed by physical vapor deposition (PVD) wherein a coating material physically deposits on the surface of the particles. Preferred coatings deposited by PVD include organic materials and elemental metals. Alternatively, the gaseous precursor can react in the gas phase forming small particles, for example less than about 5 nanometers in size, which then diffuse to the larger particle surface and sinter onto the surface, thus forming a coating. This method is referred to as gas-to-particle conversion (GPC). Whether such coating reactions occur by CVD, PVD or GPC is dependent on the reactor conditions, such as temperature, precursor partial pressure, water partial pressure and the concentration of particles in the gas stream. Another possible surface coating method is surface conversion of the surface of the particles by reaction with a vapor phase reactant to convert the surface of the glass particles to a different material than that originally contained in the particles. Silicon chlorides, alkoxides and other precursors can be used for these purposes.

As is discussed above, the glass particles can also be etched using a reactant that removes material from the surface of the particles resulting in a roughened surface. Further, the particles can be treated to silanate the surface of the particles. It is preferred to increase the number of hydroxyl groups on the particle surface prior to silanation. Therefore, the particles can be heated in a wet environment such as steam to increase the number of hydroxyl groups on the surface of the particles. This advantageously permits a higher degree of silanation when reacting the surfaces of the particles with silanating agents.

The structural modification that can occur in the particle modifier 360 may be any modification to the structure or morphology of the particles 112. The particles 112 may be annealed in the particle modifier 360 to densify the particles 112 or to partially crystallize the glass particles 112. For example, the $ZrO_2$—$SiO_2$ glass compositions according to the present invention are preferably heat treated at temperatures above about 1000° C. to fully form the glass-ceramic composition. Also, the glass particles may be annealed for a sufficient time to alter the thermal properties of the glass. Heat treatment at lower temperatures can be used to reduce adsorbed $NO_x$, or other by-product gasses.

A composite dental resin according to the present invention includes a resin and glass particles dispersed throughout the resin. The viscosities of the glass/resin composite formed with the particles disclosed herein can be greater than about 100,000 centipoise, and even greater than about 1,000,000 centipoise or higher to the point of forming a putty-like substance.

For syringe dispense, the viscosity of the composite resin must be low enough that it can be passed through a tube with a diameter on the order of several hundred micrometers. For packing putty-like filling materials, the higher ranges of viscosity are preferred.

The glass particles of the present invention advantageously permit the incorporation of higher levels of glass particles while maintaining a sufficient viscosity and good flowability for either type of filler composition. The higher glass loading leads to higher wear resistance and strength. For flowable resins used for syringe dispense, the glass particles of the present invention are preferably loaded into the resin matrix with a particle loading of at least about 50 weight percent, and more preferably at least about 60 weight percent, For more viscous putty-like compositions, the glass loading is preferably at least about 70 weight percent and more preferably at least about 85 weight percent. During manufacture, the viscous dental compositions (filler and resin) is extruded through a die and cut into short lengths. The particles of the present invention can be loaded in the composition up to 85 weight percent or higher while maintaining sufficient flow properties to be extruded.

The polymerizable resins can include dimethacrylates such as bis-GMA, a bisphenol derivative. Other components, including aspherical filler particles, can also be added to the composition.

The degree of particle loading in the resin matrix has a direct effect on strength. At low loadings the relationship is linear. However, at higher loadings the relationship deviates from linear and will finally reach a maximum. At this point the concentration of particles is so high they begin to touch. This results in internal voids and short-circuits in the path for crack growth. Thus, an optimum loading exists from the perspective of mechanical properties. The dental composition can advantageously include some non-spherical (e.g., elongated) filler to improve the mechanical properties of the composition.

It is important that a strong bond is formed between the surface of the glass particles and the resin matrix. If there is any separation or delamination this will cause voids or pores to form which degrade the opacity because light passing through the composite will be scattered by the pore surfaces. The strength of the composite will also be adversely affected because the pores will act as crack initiators. Once a crack begins to grow from one of these pores it will coalesce with other cracks to form larger cracks. These will in turn propagate to the surface of the composite to finally cause failure. Thus, the more pores or voids in the composite, the lower the strength of the composite. Thus, it is important to obtain sufficient silanation of the particle surfaces to enhance the particle to matrix bond strength. The chemical species at the glass/resin interface should be such that they provide bonding that is as strong as the matrix. This will yield a high modulus material with good fracture toughness.

Glass particles and resin must be mixed under high shear forces to cause the particles to be separated from one another. If mixing is not done properly, the particles will remain clustered and not form a complete bond with the matrix. Also, the particles need to be uniformly dispersed to maximize the strength and minimize the opacity. Particle clustering will result in deviations in the refractive index that will increase opacity. Also, voids may form which are detrimental to both strength and opacity. If the particles are uniformly dispersed, the refractive index will be constant throughout the composite. Uniform dispersion will also yield the highest strength because it will provide the most tortuous path for crack growth. Thus, agglomeration of particles in the resin should be avoided. During the processing of the resin, bubbles should also be removed. Evacuation or resin thinning are useful techniques to remove bubbles.

The refractive index of the matrix and the particles should be substantially identical to allow maximum transmission of light. Any deviation between the two will result in deflection of the direction of light at the particle-matrix interfaces ultimately causing light scattering. As this difference in refractive index increases, the opacity dramatically increases. The size of the particles can have some effect on the opacity. As the particle size approaches the wavelengths of visible light, roughly 0.5 $\mu$m, it becomes more important to match the refractive index of the glass to that of the resin.

For application purposes, it is best to have spherical particles because they will flow the best in the resin and the viscosity will be minimal. For a dentist, this is an important property so that the composite can be applied into the smallest crevices. Less force will also be required when applying and forming the resin to create shapes and surfaces necessary to conform to the shape of the tooth.

Spherical particles allow for smoother surfaces, which are best for wear. There may be less surface pullout resulting in less crack growth initiation at the surface of the composite. This could yield high fracture toughness if the surface flaws are more prone to causing failure other than the internal flaws.

The chemical and mechanical bonding between the resin and particles is also important. In both cases, a high surface area will lead to more bonds, which in turn yields higher bond strength.

EXAMPLES

A dental glass composition was produced in accordance with the present invention. The glass composition was a barium boroaluminosilicate glass (Ba—B—Al—Si—O) including 33 wt. % BaO, 5 wt. % $B_2O_3$, 2 wt. % $Al_2O_3$ and 60 wt. % $SiO_2$. The precursors were barium nitrate (Ba $(NO_3)_2$), boric acid, aluminum nitrate, and fumed $SiO_2$. The glass precursor concentration in the solution was about 5 weight percent. No heating of the precursor solution was necessary.

The precursor was atomized using ultrasonic transducers operating at a frequency of about 1.6 MHz. The carrier gas was dry air and the reaction temperature was about 1175° C. Aerosol droplets having a size of greater than about 15 $\mu$m were removed prior to entering the furnace by using an impactor.

Figure 35:
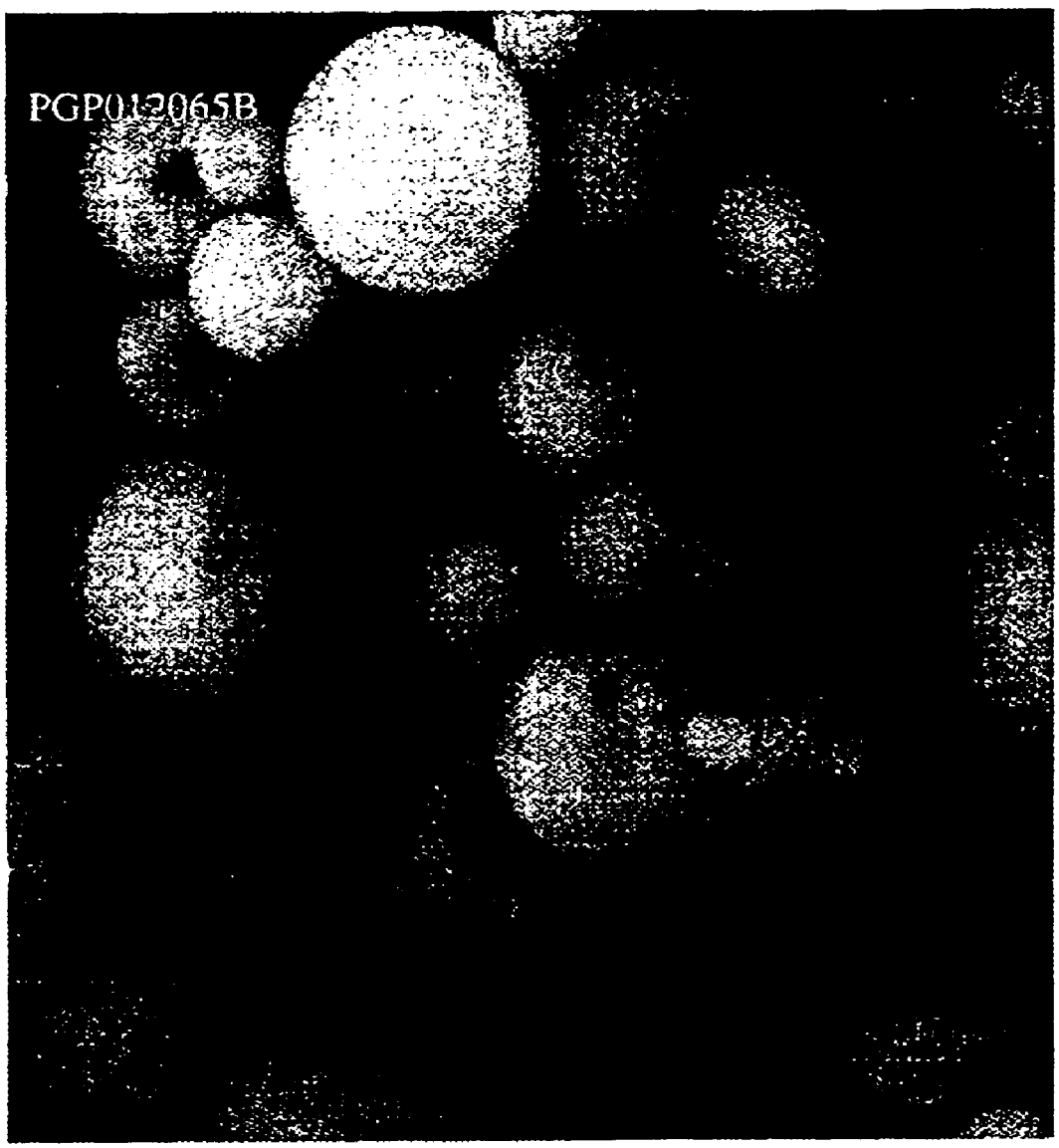
FIG. 35 illustrates an SEM photomicrograph of a glass powder batch according to an embodiment of the present invention.

The resulting glass powder had an average particle size ($d_{50}$) of about 1.4 $\mu$m and 95 weight percent of the particles had a size smaller than about 3.4 $\mu$m. The glass particles are illustrated in the SEM photomicrograph of FIG. 35.

Comparative Example

For comparison, a dental glass composition in accordance with U.S. Pat. No. 6,000,241 by Ranade et al. was prepared according to the teachings therein. Silica ($SiO_2$), aluminum nitrate ($Al(NO_3)$), boric acid and barium nitrate ($Ba(NO_3)_2$) were mixed in the amounts specified by Ranade et al., specifically 50% silica, 8% alumina, 9% $B_2O_3$ and 33% BaO. The powder was atomized by ultrasonic transducers to form droplets which were suspended in a carrier gas and passed through a furnace heated to a reaction temperature of 1000° C.

In a first example, a flow rate of gas of 2 cfm (cubic feet per minute) was used. The ultrasonic atomization system had 9 ultrasonic heads. The powder was cooled by mixing with room temperature air and then collected using a cyclone. The powder exhibited a refractive index that was outside the measurable range of 1.46 to 1.72 indicating very poor optical properties.

A second example at a flow rate of 4 cfm of gas also gave powders with the refractive index outside the measurable and useful range. The powders were observed by scanning electron microscopy to be inhomogeneous in composition for both examples. These examples indicate that these conditions can not produce particles with properties useful for dental glass application in resin composites.

Hydroxylation 400 g of spherical Ba—B—Al—Si—O glass synthesized by spray pyrolysis was mixed with 400 g of deionized water and was stirred with a magnetic stirrer for 1 hour. The slurry was placed on a Buechner funnel equipped with filter paper and some liquid was removed by applying low pressure. The remaining wet paint-like matter was transferred into a crystallization dish to form a layer less than 1 inch in height. The crystallization dish was heated in a drying oven at 115° C. for 36 hours to remove physically adsorbed water. The dried material was lightly crushed into smaller powder particles suitable for silanation. Thermogravimetric analysis indicated a doubling of the hydroxide concentration on the surface of the glass when compared to a non-treated sample. The increased $OH^-$ concentration is assumed to consist of a combination of both newly formed $OH^-$ groups on the surface and hydrogen-bonded water in the next layer. Visual examination of the flow characteristics and wetting of glass surfaces indicated that the hydroxylated sample exhibits much stronger hydrophilic characteristics than a non-treated sample.

Another 400 g sample of the spherical Ba—B—Al—Si—O glass was mixed with 60 g deionized water and kept at ambient conditions in a capped bottle for 50 hours. The powder was then placed in a drying oven at 115° C. for 16 hours. Thermogravimetric analysis of this powder indicated a smaller increase of surface hydroxide groups when compared to the foregoing example.

Silanation

Two samples each of the hydroxylated powders were treated with 1.5 wt. % and 3 wt. % methacryl 3-trismethoxysilylpropionate, respectively, and were kept for 2 hours at room temperature in closed bottles. After two hours, the powder is washed with 0.5 wt. % acetic acid solution. The liquid was removed using a Buechner funnel, and the collected powder placed in a drying oven at 90° C. for 19 hours. Evaluating the hydrophobicity of the samples prepared demonstrated a dramatic difference between the silanated samples that originate from the first and second batches. The samples having higher $OH^-$ concentration exhibited both higher flow characteristics and almost no wetting of a borosilicate surface indicating a higher degree of the silyl surface groups and possibly better uniformity.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A powder batch comprising glass particles, wherein said glass particles are substantially spherical, have a weight average particle size of from about 1 μm to about 5 μm and a surface area of at least about 5 $m^2/g$ and wherein said glass particles comprise silane groups attached to the outer surface of said particles wherein the concentration of silane groups is at least about 5 silane groups per square nanometer of glass surface area.

2. A powder batch as recited in claim 1, wherein at least about 80 weight percent of said glass particles have a size of not greater than about 2.5 times said average particle size.

3. A powder batch as recited in claim 1, wherein at least about 90 weight percent of said glass particles have a size of not greater than about 2.5 times said average particle size.

4. A powder batch as recited in claim 1, wherein said powder batch has a bimodal particle size distribution.

5. A powder batch as recited in claim 1, wherein said powder batch has a bimodal particle size distribution wherein a first mode of particles has an average particle size of from about 0.5 to 1 μm.

6. A powder batch as recited in claim 1, wherein said glass particles comprise at least about 95 weight percent glass.

7. A powder batch as recited in claim 1, wherein said glass particles have a particle density of at least about 95 percent of the theoretical density.

8. A powder batch as recited in claim 1, wherein not greater than about 1 weight percent of said glass particles are in the form of hard agglomerates.

9. A powder batch as recited in claim 1, wherein said glass is an aluminosilicate glass.

10. A powder batch as recited in claim 1, wherein said glass is an aluminosilicate glass further comprising fluorine.

11. A powder batch as recited in claim 1, wherein said glass is selected from the group consisting of calcium aluminosilicate, strontium aluminosilicate and barium aluminosilicate.

12. A powder batch as recited in claim 1, wherein said glass is a barium boroaluminosilicate glass.

13. A powder batch as recited in claim 1, wherein said glass particles comprise no greater than about 0.1 atomic percent impurities.

14. A powder batch as recited in claim 1, wherein said glass particles comprise not greater than about 100 ppm metallic impurities.

15. A powder batch as recited in claim 1, wherein said glass is an aluminosilicate glass and wherein the concentration of silica is higher near the particle surface than in the bulk of the particle.

16. A powder batch as recited in claim 1, wherein said glass particles have a surface area of at least about 10 $m^2/g$.

17. A powder batch as recited in claim 1, wherein the concentration of silane groups on the particle surface is not greater than about 3 weight percent silane based on the weight of the glass particles.

18. A powder batch as recited in claim 1, wherein the concentration of silane groups on the particle surface is not greater than about 2 weight percent silane based on the weight of the glass particles.

19. A powder batch as recited in claim 1, wherein said concentration of silane groups is at least about 7 silane groups per square nanometer.

20. A powder batch as recited in claim 1, wherein said concentration of silane groups is from about 10 to about 13 silane groups per square nanometer.

21. A powder batch as recited in claim 1, wherein said silane groups are methacryl-functional silane groups.

22. A powder batch as recited in claim 1, wherein said particles have a refractive index of from about 1.40 to about 1.60.

23. A powder batch as recited in claim 1, wherein said particles have a refractive index of from about 1.50 to 1.55.

24. A powder batch of dental glass particles wherein said glass is a barium boroaluminosilicate glass and wherein said particles are substantially spherical, have an average particle size of from about 1 μm to about 5 μm, a particle size distribution wherein at least about 80 weight percent of said glass particles have a size of not greater than about 2.5 times said average particle size and wherein the surface area of said glass particles is at least about 5 $m^2/g$.

25. A powder batch as recited in claim 24, wherein said glass has a composition comprising from about 55 to 65 weight percent $SiO_2$, from about 28 to 38 weight percent BaO, up to 10 weight percent $B_2O_3$ and up to 4 weight percent $Al_2O_3$.

26. A powder batch as recited in claim 24, wherein said particles have a density of at least about 95 percent of the theoretical density for said glass composition.

27. A powder batch as recited in claim 24, wherein said glass particles have a refractive index of from about 1.40 to about 1.60.

28. A powder batch as recited in claim 24, wherein said glass particles have a refractive index of from about 1.50 to 1.55.

29. A powder batch as recited in claim 24, wherein the concentration of silica is higher near the particle surface than in the bulk of the particle.

30. A powder batch as recited in claim 24, wherein said glass particles comprise silane groups attached to the outer surface of said particles.

31. A powder batch as recited in claim 24, wherein said glass particles comprise silane groups attached to the outer surface of said particles wherein the concentration of said silane groups is at least about 7 silane groups per square nanometer of glass surface area.

32. A powder batch as recited in claim 24, wherein said surface area is at least about 10 $m^2/g$.

33. A powder batch as recited in claim 24, wherein said glass further comprises fluorine.

* * * * *

UNITED STATES PATENT AND TRADEMARK OFFICE
CERTIFICATE OF CORRECTION

PATENT NO.     : 6,623,856 B1
DATED          : September 23, 2003
INVENTOR(S)    : Kodas et al.

It is certified that error appears in the above-identified patent and that said Letters Patent is hereby corrected as shown below:

Title page,
Item [54], Title, please delete the words "DENTAL GLASS POWDERS COMPRISING SPHERICAL GLASS PARTICLES OF SPECIFIC PARTICLE SIZE DISTRIBUTION", and insert therefor -- DENTAL GLASS POWDERS --.

Signed and Sealed this

Eighteenth Day of May, 2004

JON W. DUDAS
*Acting Director of the United States Patent and Trademark Office*